US008658791B2

(12) United States Patent
Epp et al.

(10) Patent No.: US 8,658,791 B2
(45) Date of Patent: Feb. 25, 2014

(54) 2-SUBSTITUTED-6-AMINO-5-ALKYL, ALKENYL OR ALKYNYL-4-PYRIMIDINECARBOXYLIC ACIDS AND 6-SUBSTITUTED-4-AMINO-3-ALKYL, ALKENYL OR ALKYNYL PICOLINIC ACIDS AND THEIR USE AS HERBICIDES

(75) Inventors: Jeffrey B. Epp, Noblesville, IN (US); Paul R. Schmitzer, Indianapolis, IN (US); Terry W. Balko, Greenfield, IN (US); Carla N. Yerkes, Crawfordsville, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 0 days.

(21) Appl. No.: 13/587,239

(22) Filed: Aug. 16, 2012

(65) Prior Publication Data
US 2013/0210631 A1    Aug. 15, 2013

Related U.S. Application Data

(60) Continuation of application No. 12/581,913, filed on Oct. 20, 2009, now Pat. No. 8,268,753, which is a division of application No. 12/243,469, filed on Oct. 1, 2008, now Pat. No. 7,786,044.

(60) Provisional application No. 60/997,210, filed on Oct. 2, 2007, provisional application No. 61/049,536, filed on May 1, 2008.

(51) Int. Cl.
*C07D 239/00*    (2006.01)
*A61K 31/44*    (2006.01)

(52) U.S. Cl.
USPC ............................................. 544/255; 514/349

(58) Field of Classification Search
None
See application file for complete search history.

(56) References Cited

U.S. PATENT DOCUMENTS

| 6,297,197 | B1 | 10/2001 | Fields et al. | |
| 6,784,137 | B2 | 8/2004 | Balko et al. | |
| 7,300,907 | B2 * | 11/2007 | Epp et al. | 504/239 |
| 7,314,849 | B2 | 1/2008 | Balko et al. | |
| 7,432,227 | B2 | 10/2008 | Balko et al. | |
| 7,538,214 | B2 * | 5/2009 | Epp et al. | 544/329 |
| 7,915,200 | B2 * | 3/2011 | Epp et al. | 504/239 |
| 2009/0062125 | A1 | 3/2009 | Epp et al. | |

FOREIGN PATENT DOCUMENTS

| WO | 2005/063721 | 7/2005 |
| WO | WO 2005063721 A1 * | 7/2005 |
| WO | 2007/082098 A | 7/2007 |
| WO | 2007/092184 | 8/2007 |
| WO | 2007/120706 A | 10/2007 |

* cited by examiner

*Primary Examiner* — James O Wilson
*Assistant Examiner* — Oluwafemi Masha
(74) *Attorney, Agent, or Firm* — Robert Chang

(57) ABSTRACT

6-Amino-4-pyrimidinecarboxylic acids having alkyl, alkenyl or alkynyl substituents in the 5-position and 4-aminopicolinic acids having alkyl, alkenyl or alkynyl substituents in the 3-position, and their amine and acid derivatives, are potent herbicides demonstrating a broad spectrum of weed control.

17 Claims, No Drawings

2-SUBSTITUTED-6-AMINO-5-ALKYL, ALKENYL OR ALKYNYL-4-PYRIMIDINECARBOXYLIC ACIDS AND 6-SUBSTITUTED-4-AMINO-3-ALKYL, ALKENYL OR ALKYNYL PICOLINIC ACIDS AND THEIR USE AS HERBICIDES

This application is a continuation application of U.S. Ser. No. 12/581,913 filed on Oct. 20, 2009, which is a divisional application of U.S. Ser. No. 12/243,469 filed on Oct. 1, 2008, and claims the benefit of U.S. Provisional Application Ser. No. 60/997,210 filed on Oct. 2, 2007 and U.S. Provisional Application Ser. No. 61/049,536 filed on May 1, 2008.

BACKGROUND OF THE INVENTION

This invention relates to certain novel 2-(substituted)-6-amino-5-(alkyl, alkenyl or alkynyl)-4-pyrimidine-carboxylates and 6-(substituted)-4-amino-3-(alkyl, alkenyl or alkynyl) picolinates and their derivatives and to the use of these compounds as herbicides.

A number of pyrimidine carboxylic acids and their pesticidal properties have been described in the art. WO 2005/063721 A1, WO 2007/092184 A2 and U.S. Pat. No. 7,300,907 B2 disclose a genus of 2-substituted-6-amino-4-pyrimidinecarboxylic acids and their derivatives with halogen, cyano, thiocyanato, nitro, alkyl, haloalkyl, alkoxy, thioalkyl and amino substituents in the 5-position and their use as herbicides.

A number of picolinic acids and their pesticidal properties have been described in the art. U.S. Pat. Nos. 6,297,197 B1; 6,784,137 B2; and 7,314,849 B2 and US Patent Application Publication 2004/0198608 A1 disclose a genus of 6-substituted-4-aminopicolinic acids and their derivatives with halogen, cyano, thiocyanato, nitro, alkyl, haloalkyl, alkoxy, haloalkoxy, thioalkyl and aryloxy substituents in the 3-position and their use as herbicides.

SUMMARY OF THE INVENTION

It has now been found that certain 2-(substituted)-6-amino-5-(alkyl, alkenyl or alkynyl)-4-pyrimidinecarboxylic acids and 6-(substituted)-4-amino-3-(alkyl, alkenyl or alkynyl) picolinic acids and their derivatives are superior herbicides with a broad spectrum of weed control against woody plants, grasses and sedges as well as broadleaf weeds and with excellent selectivity to beneficial plant species. The compounds further possess excellent toxicological or environmental profiles.

The invention includes compounds of Formula I:

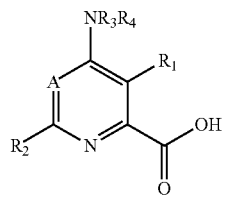

I wherein
A represents N or $CR_5$;
$R_1$ represents $C_1$-$C_4$ alkyl, $C_1$-$C_4$ haloalkyl, $C_2$-$C_4$ alkoxyalkyl, $C_2$-$C_4$ alkylthioalkyl, $C_2$-$C_4$ alkenyl, $C_2$-$C_4$ haloalkenyl, $C_2$-$C_4$ alkoxyalkenyl, $C_2$-$C_4$ thioalkylalkenyl, $C_2$-$C_4$ alkynyl or $C_2$-$C_4$ haloalkynyl, formyl, $C_2$-$C_4$ alkylcarbonyl, $C_2$-$C_4$ haloalkylcarbonyl;

$R_2$ represents $C_1$-$C_6$ alkyl, $C_1$-$C_6$ haloalkyl, $C_2$-$C_6$ alkenyl, $C_2$-$C_6$ haloalkenyl or

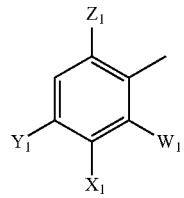

wherein
$W_1$ represents H or halogen;
$X_1$ represents H, halogen, nitro, cyano, formyl, $C_1$-$C_6$ alkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_2$-$C_6$ halo-alkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ halo-alkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —C(O)O$R_7$, —C(O)N$R_6R_7$, —C$R_6$NO$R_7$, —N$R_6R_7$, —N$R_6$O$R_7$, —N$R_6$SO$_2R_7$, —N$R_6$C(O)$R_7$, —N$R_6$C(O)O$R_7$, —N$R_6$C(O)N$R_6R_7$ or —NC$R_6$N$R_6R_7$;
$Y_1$ represents H, halogen, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl or $C_2$-$C_6$ haloalkenyl, or, when $X_1$ and $Y_1$ are taken together, represents —O(CH$_2$)$_n$CH$_2$—, or —O(CH$_2$)$_n$O— wherein n=1 or 2; and
$Z_1$ represents H or halogen;
$R_3$ and $R_4$ independently represent H, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl or $C_1$-$C_6$ dialkyl phosphonyl or $R_3$ and $R_4$ taken together with N represent a 5- or 6-membered saturated ring; and
$R_5$ represents H or halogen;
$R_6$ represents H, $C_1$-$C_4$ alkyl or $C_1$-$C_4$ haloalkyl; and
$R_7$ represents $C_1$-$C_4$ alkyl or $C_1$-$C_4$ haloalkyl;
and agriculturally acceptable derivatives of the carboxylic acid group.

Preferred compounds of formula (I) include the following classes:

(1) Compounds of formula (I) wherein $R_1$ is $C_1$-$C_2$ alkyl, $C_1$-$C_2$ haloalkyl, $C_2$-$C_3$ alkenyl or $C_2$-$C_3$ haloalkenyl, most preferably wherein $R_1$ is vinyl.

(2) Compounds of formula (I) wherein $R_2$ is cyclopropyl.

(3) Compounds of formula (I) wherein $R_2$ is

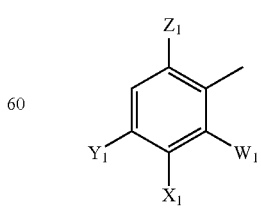

(4) Compounds of class (3) wherein $W_1$ represents H or F, $X_1$ represents H, halogen, $C_1$-$C_4$ alkyl, $C_1$-$C_4$ haloalkyl, $C_1$-$C_4$ alkoxy, $C_1$-$C_4$ haloalkoxy or —$NR_6R_7$, $Y_1$ represents Cl or halomethyl, and $Z_1$ represents H or F.

(5) Compounds of formula (I) wherein $R_3$ and $R_4$ are H or $C_1$-$C_6$ alkyl.

It will be appreciated by those skilled in the art that the most preferred compounds are generally those which are comprised of combinations of the above preferred classes.

The invention includes herbicidal compositions comprising an herbicidally effective amount of a compound of Formula I and agriculturally acceptable derivatives of the carboxylic acid group in a mixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil prior to emergence of the vegetation.

DETAILED DESCRIPTION OF THE INVENTION

The herbicidal compounds of the present invention are derivatives of 6-amino-5-(alkyl, alkenyl or alkynyl)-4-pyrimidinecarboxylic acids or 4-amino-3-(alkyl, alkenyl or alkynyl) picolinic acids of the formula:

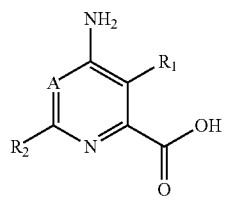

Ia wherein

A represents N or $CR_5$;

$R_1$ represents $C_1$-$C_4$ alkyl, $C_1$-$C_4$ haloalkyl, $C_2$-$C_4$ alkoxyalkyl, $C_2$-$C_4$ alkylhioalkyl, $C_2$-$C_4$ alkenyl, $C_2$-$C_4$ haloalkenyl, $C_2$-$C_4$ alkoxyalkenyl, $C_2$-$C_4$ thioalkylalkenyl, $C_2$-$C_4$ alkynyl or $C_2$-$C_4$ haloalkynyl, formyl, $C_2$-$C_4$ alkylcarbonyl, $C_2$-$C_4$ haloalkylcarbonyl;

$R_2$ represents $C_1$-$C_6$ alkyl, $C_1$-$C_6$ haloalkyl, $C_2$-$C_6$ alkenyl, $C_2$-$C_6$ haloalkenyl or

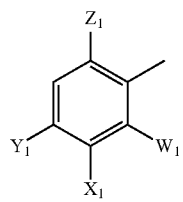

wherein $W_1$ represents H or halogen;

$X_1$ represents H, halogen, nitro, cyano, formyl, $C_1$-$C_6$ alkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylhio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ halo-alkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —$C(O)OR_7$, —$C(O)NR_6R_7$, —$CR_6NOR_7$, —$NR_6R_7$, —$NR_6OR_7$, —$NR_6SO_2R_7$, —$NR_6C(O)R_7$, —$NR_6C(O)OR_7$, —$NR_6C(O)NR_6R_7$ or —$NCR_6NR_6R_7$;

$Y_1$ represents H, halogen, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl or $C_2$-$C_6$ haloalkenyl, or, when $X_1$ and $Y_1$ are taken together, represents —$O(CH_2)_nCH_2$—, or —$O(CH_2)_nO$— wherein n=1 or 2; and $Z_1$ represents H or halogen;

$R_5$ represents H or halogen $R_6$ represents H, $C_1$-$C_4$ alkyl or $C_1$-$C_4$ haloalkyl; and $R_7$ represents $C_1$-$C_4$ alkyl or $C_1$-$C_4$ haloalkyl;

The amino group at the 6-position of the pyrimidine ring or the 4-position of the pyridine ring can be unsubstituted or substituted with one or more $C_1$-$C_6$ alkyl, $C_3$-$C_6$ alkenyl, $C_3$-$C_6$ alkynyl, hydroxy, $C_1$-$C_6$ alkoxy or amino substituents. The amino group can be further derivatized as an amide, a carbamate, a urea, a sulfonamide, a silylamine or a phosphoramidate. Such derivatives are capable of breaking down into the amine. An unsubstituted amino group or one substituted with one or two alkyl substituents is preferred.

The carboxylic acids of Formula Ia are believed to be the compounds that actually kill or control undesirable vegetation and are typically preferred. Analogs of these compounds in which the acid group of the pyrimidine carboxylic acid or picolinic acid is derivatized to form a related substituent that can be transformed within plants or the environment to an acid group possess essentially the same herbicidal effect and are within the scope of the invention. Therefore, an "agriculturally acceptable derivative", when used to describe the carboxylic acid functionality at the 4-position of the pyrimidine ring or the 2-position of the pyridine ring, is defined as any salt, ester, acylhydrazide, imidate, thioimidate, amidine, amide, orthoester, acylcyanide, acyl halide, thioester, thionoester, dithiolester, nitrile or any other acid derivative well known in the art which (a) does not substantially affect the herbicidal activity of the active ingredient, i.e., the 2-(substituted)-6-amino-5-(alkyl, alkenyl or alkynyl)-4-pyrimidinecarboxylic acid or the 6-(substituted)-4-amino-3-(alkyl, alkenyl or alkynyl) picolinic acid, and (b) is or can be hydrolyzed, oxidized or metabolized in plants or soil to the 4-pyrimidinecarboxylic acid or the picolinic acid of Formula Ia that, depending upon the pH, is in the dissociated or the undissociated form. The preferred agriculturally acceptable derivatives of the carboxylic acid are agriculturally acceptable salts, esters and amides. Likewise, an "agriculturally acceptable derivative", when used to describe the amine functionality at the 6- or 4-position, is defined as any salt, silylamine, phosphorylamine, phosphinimine, phosphoramidate, sulfonamide, sulfilimine, sulfoximine, aminal, hemiaminal, amide, thioamide, carbamate, thiocarbamate, amidine, urea, imine, nitro, nitroso, azide, or any other nitrogen containing derivative well known in the art which (a) does not substantially affect the herbicidal activity of the active ingredient, i.e., the 2-(substituted)-6-amino-5-(alkyl, alkenyl or alkynyl)-4-pyrimidinecarboxylic acid or the 6-(substituted)-4-amino-3-(alkyl, alkenyl or alkynyl) picolinic acid, and (b) is or can be hydrolyzed in plants or soil to a free amine. N-Oxides which are also capable of breaking into the parent pyrimidine or pyridine are also covered by the scope of this invention.

Suitable salts include those derived from alkali or alkaline earth metals and those derived from ammonia and amines. Preferred cations include sodium, potassium, magnesium, and aminium cations of the formula:

$R_8R_9R_{10}NH^+$ wherein $R_8$, $R_9$ and $R_{10}$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R_8$, $R_9$ and $R_{10}$ are sterically compatible. Additionally, any two of $R_8$, $R_9$ and $R_{10}$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethyl-amine, morpholine, cyclododecylamine, or benzylamine. Amine salts are often preferred forms of the compounds of Formula I because they are water-soluble and lend themselves to the preparation of desirable aqueous based herbicidal compositions.

Suitable esters include those derived from $C_1$-$C_{12}$ alkyl, $C_3$-$C_{12}$ alkenyl or $C_3$-$C_{12}$ alkynyl alcohols, such as methanol, iso-propanol, butanol, 2-ethylhexanol, butoxyethanol, methoxypropanol, allyl alcohol, propargyl alcohol or cyclohexanol. Esters can be prepared by coupling of the 4-pyrimidine carboxylic acids or picolinic acids with the alcohol using any number of suitable activating agents such as those used for peptide couplings such as dicyclohexylcarbodiimide (DCC) or carbonyl diimidazole (CDI), by reacting the corresponding acid chloride of a 4-pyrimidinecarboxylic acid or picolinic acid of Formula I with an appropriate alcohol, by reacting the corresponding 4-pyrimidinecarboxylic acid or picolinic acid of Formula I with an appropriate alcohol in the presence of an acid catalyst or by transesterification. Suitable amides include those derived from ammonia or from $C_1$-$C_{12}$ alkyl, $C_3$-$C_{12}$ alkenyl or $C_3$-$C_{12}$ alkynyl mono- or di-substituted amines, such as but not limited to dimethylamine, diethanolamine, 2-methylthiopropylamine, bisallylamine, 2-butoxyethylamine, cyclododecylamine, benzylamine or cyclic or aromatic amines with or without additional heteroatoms such as but not limited to aziridine, azetidine, pyrrolidine, pyrrole, imidazole, tetrazole or morpholine. Amides can be prepared by reacting the corresponding 4-pyrimidinecarboxylic acid or picolinic acid chloride, mixed anhydride, or carboxylic ester of Formula I with ammonia or an appropriate amine.

The terms "alkyl", "alkenyl" and "alkynyl", as well as derivative terms such as "alkoxy", "acyl", "alkylthio" and "alkylsulfonyl", as used herein, include within their scope straight chain, branched chain and cyclic moieties. The terms "alkenyl" and "alkynyl" are intended to include one or more unsaturated bonds.

The term "aryl", as well as derivative terms such as "aryloxy", refers to a phenyl.

Unless specifically limited otherwise, the term "halogen" including derivative terms such as "halo" refers to fluorine, chlorine, bromine, and iodine.

The terms "haloalkyl," "haloalkoxy" and "haloalkylthio" refer to alkyl and alkoxy groups substituted with from 1 to the maximum possible number of halogen atoms.

The compounds of Formula I can be made using well-known chemical procedures. Many procedural details for making compounds of Formula I can be found in the following patent applications: WO 2007/082076 A1; WO 2005/063721 A1; U.S. Pat. Nos. 7,300,907 B2; 6,297,197 B1; 6,784,137 B2; 7,314,849 B2; and US Patent Application Publication 2004/0198608 A1. Intermediates not specifically mentioned in the above patent applications are either commercially available, can be made by routes disclosed in the chemical literature, or can be readily synthesized from commercial starting materials utilizing standard procedures.

As shown in Scheme 1, many 2-(substituted)-6-amino-5-(alkyl, alkenyl or alkynyl)-4-pyrimidinecarboxylic acid esters or 6-(substituted)-4-amino-3-(alkyl, alkenyl or alkynyl) picolinic acid esters of Formula I can be prepared by reaction of an appropriately substituted 5-halopyrimidine or 3-halopyridine of Formula II and an organometallic compound of type III in an inert solvent in the presence of a transition metal catalyst.

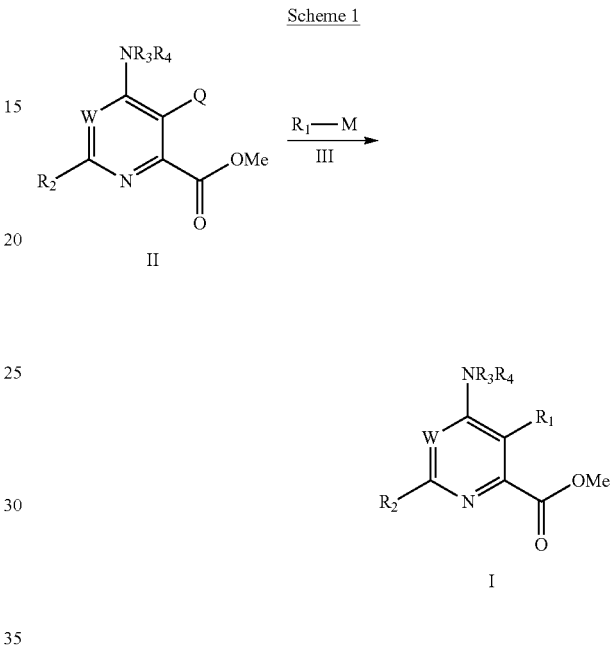

Scheme 1

In this case W can be N or $CR_5$; Q can be chlorine, bromine or iodine; $R_1$ can be alkyl, haloalkyl, alkenyl, haloalkenyl, or alkynyl group; and M can be tri-($C_1$-$C_4$ alkyl)tin or $B(OR_{11})(OR_{12})$, where $R_{11}$ and $R_{12}$ are independent of one another, hydrogen, $C_1$-$C_6$ alkyl, or when taken together form an ethylene or propylene group; and "Catalyst" can be a transition metal catalyst, in particular a palladium catalyst such as bis(triphenylphosphine) palladium(II) dichloride. The method of Scheme 1 is illustrated in Examples 17, 18, 21, 22, 24, 25, 27, 28, and 30.

As shown in Scheme 2, many 2-(substituted)-6-amino-5-halo-4-pyrimidinecarboxylic acid esters of Formula II can be made from compounds of Formula IV by reaction with a halogenating reagent such as N-bromosuccinimide in a solvent such as chloroform or acetonitrile. In this case, Q can be chlorine, bromine or iodine. The method of Scheme 2 is illustrated in Example 16.

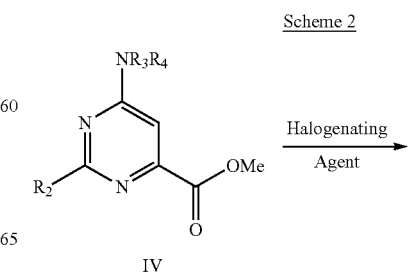

Scheme 2

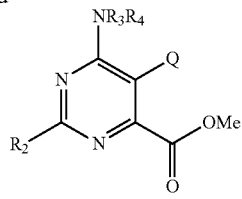

As shown in Scheme 3, many 2-(substituted)-6-amino-4-pyrimidinecarboxylic acid esters of Formula I and IV can be prepared by reaction of appropriately substituted 2-chloropyrimidines of Formula V and VI and an organometallic compound of type VII in an inert solvent in the presence of a transition metal catalyst.

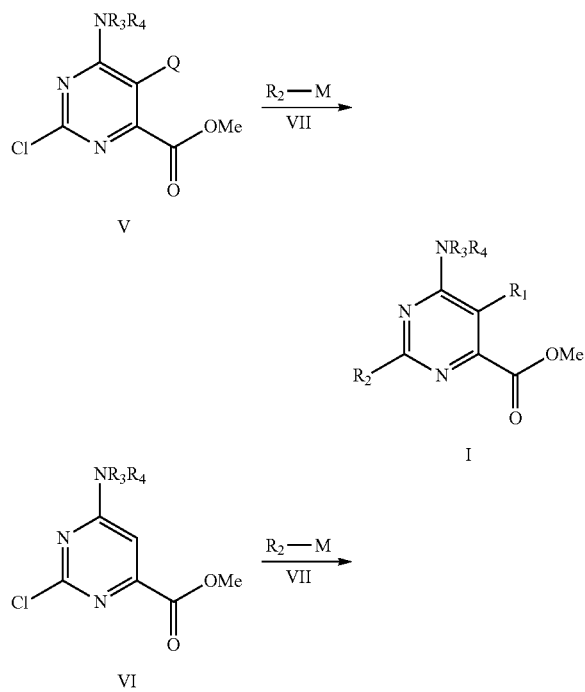

In this case $R_1$ can be an alkyl, haloalkyl, alkenyl, haloalkenyl, or alkynyl group; $R_2$ can be an alkyl, haloakyl, alkenyl, haloalkenyl or aryl group; M can be tri-($C_1$-$C_4$ alkyl)tin or B($OR_{11}$)($OR_{12}$), where $R_{11}$ and $R_{12}$ are independent of one another, hydrogen, $C_1$-$C_6$ alkyl, or when taken together form an ethylene or propylene group; and "Catalyst" can be a transition metal catalyst, in particular a palladium catalyst such as bis(triphenylphosphine) palladium(II) dichloride. The methods of Scheme 3 are illustrated in Examples 15 and 19.

As shown in Scheme 4, many 2-chloro-6-amino-5-alkyl, alkenyl or alkynyl-4-pyrimidinecarboxylic acid esters of Formula V can be obtained by reaction of appropriately substituted pyrimidines of Formula VIII and an organometallic compound of type III in an inert solvent in the presence of a transition metal catalyst.

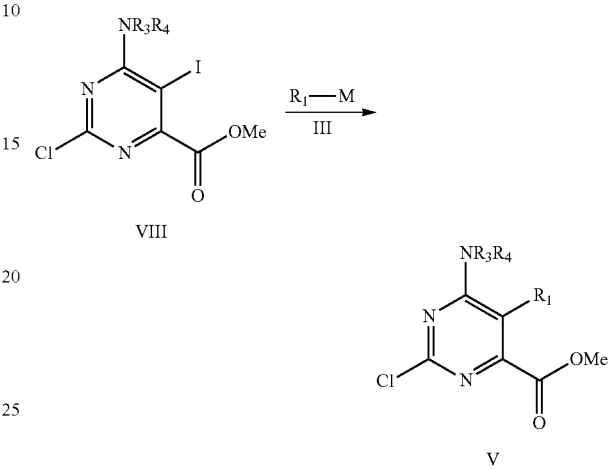

In this case $R_1$ can be an alkyl, haloalkyl, alkenyl, haloalkenyl or alkynyl group; M can be tri-($C_1$-$C_4$ alkyl)tin or B($OR_{11}$)($OR_{12}$), where $R_{11}$ and $R_{12}$ are independent of one another, hydrogen, $C_1$-$C_6$ alkyl, or when taken together form an ethylene or propylene group; and "Catalyst" can be a transition metal catalyst, in particular a palladium catalyst such as bis(triphenylphosphine)-palladium(II) dichloride. The method of Scheme 4 is illustrated in Example 13.

As shown in Scheme 5, many 2-chloro-6-amino-5-iodo-4-pyrimidinecarboxylic acid esters pyrimidines of Formula VIII can be obtained by reaction of pyrimidines of Formula IX with amines of type X. Pyrimidines of Formula IX can be prepared from compounds of Formula XI by reaction with reagents such as phosphorous oxychloride either neat or in the presence of a catalytic amount of dimethylformamide. The methods of Scheme 5 are illustrated in Examples 11 and 12.

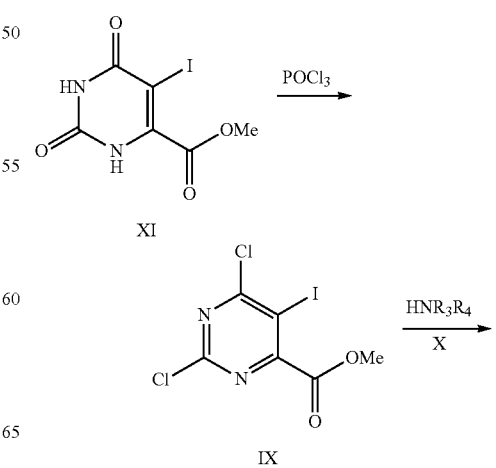

-continued

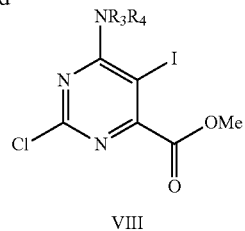

VIII

It is recognized that some reagents and reaction conditions disclosed herein or in the chemical literature for preparing compounds of Formula I may not be compatible with certain functionalities present in the intermediates. In these instances, the incorporation of protection/deprotection sequences or functional group interconversions into the synthesis will aid in obtaining the desired products. The use and choice of the protection groups will be apparent to one skilled in chemical synthesis.

One skilled in the art will recognize that, in some cases, after the introduction of a given reagent as disclosed herein or in the chemical literature, it may be necessary to perform additional routine synthetic steps not described in detail to complete the synthesis of compounds of Formula I. One skilled in the art will also recognize that it may necessary to perform a combination of the steps disclosed herein or in the chemical literature in an order other than that implied by the particular sequence presented to prepare the compounds of Formula I.

Finally, one skilled in the art will also recognize that compounds of Formula I and the intermediates described herein or in the chemical literature can be subjected to various electrophilic, nucleophilic, radical, organometallic, oxidation, and reduction reactions to add substituents or modify existing substituents.

The compounds of Formula I have been found to be useful as pre-emergence and post-emergence herbicides. They can be employed at non-selective (higher) rates of application to control a broad spectrum of the vegetation in an area or at lower rates of application for the selective control of undesirable vegetation. Areas of application include pasture and rangelands, roadsides and rights of way, power lines and any industrial areas, as well as turf and ornamental environments where control of undesirable vegetation is desirable. Another use is the control of unwanted vegetation in crops such as corn, rice and cereals. They can also be used to control undesirable vegetation in tree crops such as citrus, apple, rubber, oil palm, forestry and others. It is usually preferred to employ the compounds postemergence. It is further usually preferred to use the compounds to control a wide spectrum of woody plants, broadleaf and grass weeds, and sedges. Use of the compounds to control undesirable vegetation in established crops is especially indicated. While each of the 2-(substituted)-6-amino-5-(alkyl, alkenyl or alkynyl)-4-pyrimidinecarboxylate and 6-(substituted)-4-amino-3-(alkyl, alkenyl or alkynyl) picolinic compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I postemergence to relatively immature undesirable vegetation to achieve the maximum control of weeds.

Application rates of about 1 to about 1,000 g/Ha are generally employed in postemergence operations; for preemergence applications, rates of about 10 to about 2,000 g/Ha are generally employed. The higher rates designated generally give non-selective control of a broad variety of undesirable vegetation. The lower rates typically give selective control and can be employed in the locus of crops.

The herbicidal compounds of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac. The herbicidal compounds of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The compounds of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyrdiethyl, MG 191, MON 4660, naphthalic anhydride (NA), oxabetrinil, R29148 and N-phenyl-sulfonylbenzoic acid amides, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are acetolactate synthase inhibitors in sensitive plants can be treated. Many glyphosate and glufosinate tolerant crops can be treated as well, alone or in combination with these herbicides. Some crops (e.g. cotton) have been made tolerant to auxinic herbicides such as 2,4-dichlorophenoxyacetic acid. These herbicides may be used to treat such resistant crops or other auxin tolerant crops.

While it is possible to utilize the 2-(substituted)-6-amino-5-(alkyl, alkenyl or alkynyl)-4-pyrimidinecarboxylate and 6-(substituted)-4-amino-3-(alkyl, alkenyl or alkynyl) picolinate compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecylbenzene-sulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be form-ulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, diffusion in standing water, by addition to irrigation water, and by other conventional means known to those skilled in the art.

The following Examples are presented to illustrate the various aspects of this invention and should not be construed as limitations to the claims.

EXAMPLES

1. Preparation of 4-Chloro-2,5-difluorophenylamine

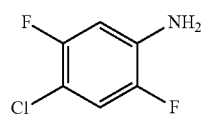

Tin (II) chloride dihydrate (15.5 g, 68.7 mmol) was dissolved in ethyl acetate (50 mL) and 1-chloro-2,5-difluoro-4-nitrobenzene (2.65 g, 13.7 mmol) was added dropwise. The reaction mixture was then stirred at 70° C. for 1 h. The reaction mixture was then carefully added to saturated aqueous sodium bicarbonate and extracted with ethyl acetate. The organic phase was washed several more times with water, dried, filtered, concentrated and purified by flash chromatography on silica gel (hexane/diethyl ether) to give the title compound as a white solid (1.65 g, 73.9% yield): ¹H NMR (CDCl₃) δ 7.02 (dd, 1H), 6.57 (dd, 1H), 3.81 (br s, 2H).

2. Preparation of 1-Bromo-4-chloro-2,5-difluorobenzene

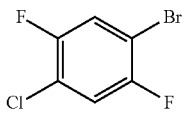

Anhydrous copper (II) bromide (2.7 g, 12.1 mmol) and t-butyl nitrite (1.56 g, 15.1 mmol) were combined in anhydrous acetonitrile (25 mL). The resulting mixture was heated to 65° C. and a solution of 4-chloro-2,5-difluoro-phenylamine (1.65 g, 10.1 mmol) in anhydrous acetonitrile (2 mL) was added dropwise (vigorous gas evolution was noted). After the reaction mixture cooled to ambient temperature, it was added to 2N HCl and extracted twice with diethyl ether. The organic extracts were then combined, washed with 2N HCl, washed with saturated sodium bicarbonate, dried, concentrated and purified by flash chromatography on silica gel (hexanes) to give the title compound as a white solid (1.11 g, 48.4% yield): ¹H NMR (CDCl₃) δ 7.38 (dd, 2H), 7.21 (dd, 2H).

3. Preparation of 2-(4-Chloro-2,5-difluorophenyl)-4,4,5,5-tetramethyl-1,3,2-dioxaborolane

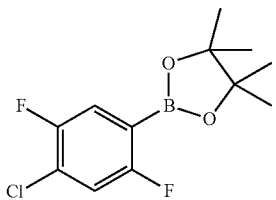 [SMILES: CC1(C)OB(c2cc(F)c(Cl)cc2F)OC1(C)C]

1-Bromo-4-chloro-2,5-difluorobenzene (1.11 g, 4.9 mmol) was dissolved in tetrahydrofuran (THF; 15 mL) and cooled to −10° C. A 2.0M solution of isopropyl-magnesium chloride (2.7 mL, 5.4 mmol) in THF was added dropwise via syringe. The reaction mixture was stirred at −10° C. for 1 h, allowed to warm toward 0° C. for 1 h, then cooled again to −10° C. A solution of 2-isopropoxy-4,4,5,5-tetramethyl-1,3,2-dioxaborolane (1.0 g, 5.4 mmol) in THF (1.0 mL) was then added dropwise and the reaction mixture was allowed to warm to ambient temperature. The reaction mixture was then added to diethyl ether and extracted with 1N sodium hydroxide twice. The aqueous phases were combined, acidified to pH 3 with concentrated HCl, and extracted with dichloromethane twice. The organic phases were combined, dried, filtered and concentrated to give the title compound (0.97 g, 72.3% yield) that was used without further purification: ¹H NMR (CDCl₃) δ 7.45 (dd, 1H), 7.09 dd, 1H), 1.36 (s, 12H).

Another compound prepared by the procedure of Example 3 is:

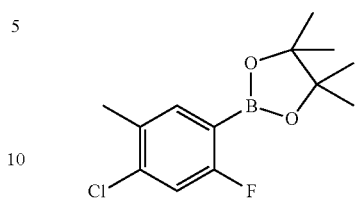

2-(4-Chloro-2-fluoro-5-methylphenyl)-4,4,5,5-tetramethyl-1,3,2-dioxaborolane: ¹H NMR (CDCl₃) δ 7.58 (d, 1H), 7.03 (d, 1H), 2.32 (s, 3H), 1.35 (s, 12H).

4. Preparation of 1-(5-Bromo-2-chlorophenyl)-ethanol

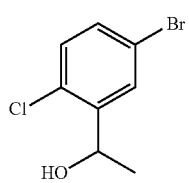

Sodium borohydride (1.182 g, 51.4 mmol) was added to a stirred solution of 1-(5-bromo-2-chlorophenyl)ethanone (10 g, 42.8 mmol) in methanol at 0° C. The resulting bubbling white mixture was allowed to warm to ambient temperature and stirred for 2 h. The reaction mixture was quenched with acetone (50 mL) and concentrated by rotary evaporation. The residue was partitioned between ethyl acetate and water. The organic phase was dried and concentrated to yield the title compound (10 g, 99% yield) as a white solid: ¹H NMR (CDCl₃) δ 7.75 (d, 1H), 7.32 (m, 1H), 7.19 (m, 1H), 5.23 (q, 1H), 1.95 (d, 1H), 1.48 (d, 3H).

Another compound prepared by the procedure of Example 4 is:

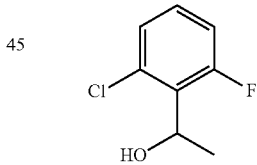

1-(2-Chloro-6-fluorophenyl)ethanol: ¹H NMR (300 MHz, CDCl₃) δ 7.14-7.22 (m, 2H), 6.99 (m, 1H), 5.38 (m, 1H), 2.48 (m, 1H), 1.63 (dd, 3H, J=1, 7 Hz).

5. Preparation of 4-Bromo-1-chloro-2-(1-fluoroethyl)-benzene

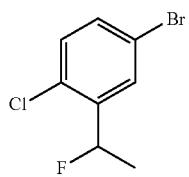

Bis(2-methoxyethyl)aminosulfur trifluoride (4.5 g, 20.34 mmol) was added to a stirred solution of 1-(5-bromo-2-chlorophenyl)ethanol (3.99 g, 16.95 mmol) in dichloromethane (50 mL) at 0° C. The resulting solution was stirred at 0° C. for 3 h. The reaction mixture was quenched with a 5% solution of aqueous sodium bicarbonate (100 mL) and the resulting bubbling biphasic reaction mixture was vigorously stirred at 0° C. for 15 min. The reaction mixture was diluted with water (50 mL) and extracted with dichloromethane twice. The combined organic layers were washed with 1M hydrochloric acid, dried and concentrated by rotary evaporation. The product was purified by flash chromatography on silica gel (hexanes) to yield the title compound (2.65 g, 11.16 mmol, 65.8% yield) as a clear oil: $^1$H NMR (CDCl$_3$) δ 7.65 (d, 1H), 7.37 (m, 1H), 7.20 (m, 1H), 5.88 (dq, 1H), 1.61 (dd, 3H).

Another compound prepared by the procedure of Example 5 is:

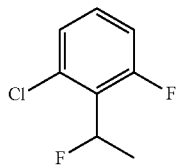

1-Chloro-3-fluoro-2-(1-fluoroethyl)benzene: $^1$H NMR (300 MHz, CDCl$_3$) δ 7.15-7.26 (m, 2H), 7.02 (m, 1H), 6.12 (dq, 1H, J=6, 46 Hz), 1.76 (ddd, 3H, J=1, 7, 23 Hz).

6. Preparation of 1-Chloro-2-difluoromethoxy-3-fluorobenzene

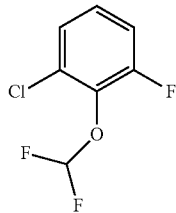 [SMILES: Fc1cccc(Cl)c1OC(F)F]

2-Chloro-6-fluorophenol (1.8 g, 12.33 mmol) was dissolved in dimethylformamide (DMF; 22 mL) and water (2.2 mL). Potassium carbonate (2.55 g, 18.5 mmol) and sodium chlorodifluoroacetate (4.7 g, 30.8 mmol) were then added and the solution was heated to 100° C. for 3 h. The cooled reaction mixture was then diluted with concentrated HCl (10 mL) and the resulting solution was stirred for 2 h. The reaction mixture was diluted with diethyl ether, washed with water, washed twice with 1M NaOH, washed once with brine, dried, filtered and concentrated under vacuum to yield the title compound (1 g, 41% yield) that was used in subsequent reactions without further purification.

7. Preparation of 2-[4-Chloro-3-(1-fluoroethyl)phenyl]-4,4,5,5-tetramethyl-1,3,2-dioxaborolane

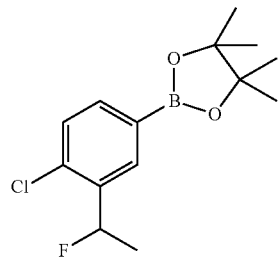 [SMILES: CC(F)c1cc(B2OC(C)(C)C(C)(C)O2)ccc1Cl]

4-Bromo-1-chloro-2-(1-fluoroethyl)benzene (2.55 g, 10.74 mmol) was dissolved in dry diethyl ether (50 mL) and cooled to −75° C. n-Butyllithium (4.72 mL, 11.81 mmol) was added dropwise keeping the temperature below −70° C. The reaction mixture was then stirred for 15 min, then 2-isopropoxy-4,4,5,5-tetramethyl-1,3,2-dioxaborolane (2.197 g, 11.81 mmol) was added and the reaction mixture was allowed to warm to ambient temperature. The reaction mixture was then diluted with water and diethyl ether. The aqueous phase was acidified with 12N HCl and the product was then extracted with diethyl ether. The organic phase was dried and concentrated under vacuum to yield the title compound (1.55 g, 5.45 mmol, 50.7% yield) as a white solid: $^1$H NMR (CDCl$_3$) δ 7.94 (d, 1H), 7.65 (m, 1H), 7.36 (m, 1H), 5.96 (dq, 1H), 1.64 (dd, 3H), 1.34 (s, 12H).

Another compound prepared by the procedure of Example 7 is:

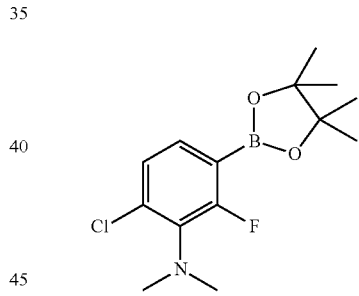

[6-Chloro-2-fluoro-3-(4,4,5,5-tetramethyl-1,3,2-dioxaborolan-2-yl)phenyl]-dimethylamine: $^1$H NMR (CDCl$_3$) δ 7.35 (m, 1H), 7.13 (m, 1H), 2.85 (d, 6H), 1.36 (s, 12H).

8. Preparation of 2-(4-Chloro-2,3-difluorophenyl)-4,4,5,5-tetramethyl-1,3,2-dioxaborolane

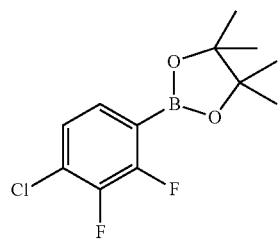 [SMILES: CC1(C)OB(c2ccc(Cl)c(F)c2F)OC1(C)C]

A 2.5M solution of n-butyllithium (2.69 ml, 6.73 mmol) in hexanes was added dropwise to a solution of 1-chloro-2,3-difluorobenzene (1 g, 6.73 mmol) in THF (25 mL) cooled to −78° C. After 45 min at −78° C., 2-isopropoxy-4,4,5,5-tetramethyl-1,3,2-dioxaborolane (1.253 g, 6.73 mmol) was added dropwise after which the reaction mixture was allowed to warm to ambient temperature. The reaction mixture was diluted with water and ethyl acetate, and the organic phase was extracted twice with water. The aqueous extracts were combined, acidified with 12N HCl to pH 3, and extracted with ethyl acetate. The organic extract was dried and concentrated under vacuum to yield the title compound as an oil product (0.93 g, 50% yield): $^1$H NMR (CDCl$_3$) δ 7.42 (m, 1H), 7.17 (m, 1H), 1.37 (s, 12H).

Another compound prepared by the procedure of Example 8 is:

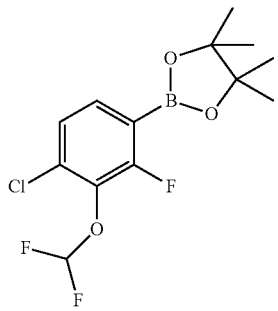 [SMILES: CC1(C)OB(c2ccc(Cl)c(OC(F)F)c2F)OC1(C)C]

2-(4-Chloro-3-difluoromethoxy-2-fluorophenyl)-4,4,5,5-tetramethyl-1,3,2-dioxaborolane: $^1$H NMR (CDCl$_3$) δ 7.1 (m, 1H), 7.02 (m, 1H), 6.8 (t, 1H), 1.23 (s, 12H).

9. Preparation of 2-(4-Chloro-2-fluoro-3-(1-fluoroethyl)phenyl)-4,4,5,5-tetramethyl-1,3,2-dioxaborolane

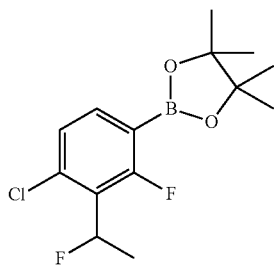 [SMILES: CC(F)c1c(Cl)ccc(B2OC(C)(C)C(C)(C)O2)c1F]

A 2.5M solution of n-butyllithium (13 mL, 33 mmol) was added to a stirred solution of diisopropylamine (5.0 mL, 35 mmol) in THF (50 mL) at −78° C. The resulting colorless solution was stirred at −78° C. for 20 min, warmed to 0° C. for 20 min, and then cooled back to −78° C. for 20 min A solution of 1-chloro-3-fluoro-2-(1-fluoroethyl)benzene (4.8 g, 27 mmol, 1.0 equiv) in THF (20 mL) at −78° C. was transferred to the base solution via cannula. The resulting dark brown solution was stirred at −78° C. for 2 h. 2-Isopropoxy-4,4,5,5-tetramethyl-1,3,2-dioxaborolane (8.3 mL, 41 mmol, 1.5 equiv) was added and the brown solution was slowly warmed to 23° C. over 20 h. The reaction mixture was diluted with 0.1M hydrochloric acid (300 mL) and extracted with dichloromethane thrice. The combined organic extracts were dried, filtered and concentrated by rotary evaporation to afford the title compound as a brown oil that solidified into a semi-solid upon standing (7.7 g, 94% yield). $^1$H NMR (300 MHz, CDCl$_3$) δ 7.62 (m, 1H), 7.17 (m, 1H), 6.13 (dq, 1H, J=6, 46 Hz), 1.75 (ddd, 3H, J=1, 7, 23 Hz), 1.36 (s, 12 H).

10. Preparation of 5-Iodo-2,6-dioxo-1,2,3,6-tetrahydropyrimidine-4-carboxylic acid methyl ester

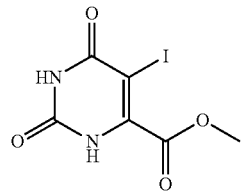

Methyl orotate (20.0 g, 118 mmol) was combined with iodine (12.8 g, 50 mmol) and periodic acid (4.8 g, 21 mmol) in methanol (250 mL) and heated at reflux for 20 h. After cooling to ambient temperature, the volatiles were removed by rotary evaporation. The solid residue was slurried in water, collected by filtration, washed well with water and dried under vacuum at 70° C. to provide the title compound (34 g, 97% yield) as a solid. It was used without further purification. MS: m/z=296.

11. Preparation of 2,6-Dichloro-5-iodopyrimidine-4-carboxylic acid methyl ester

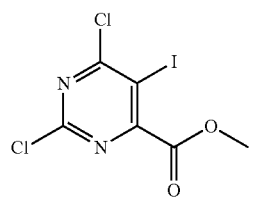

5-Iodo-2,6-dioxo-1,2,3,6-tetrahydropyrimidine-4-carboxylic acid methyl ester (5.0 g, 17 mmol) was added to POCl$_3$ (30 mL), treated with 0.5 mL DMF and heated to reflux for 3 h. The excess POCl$_3$ was removed under vacuum and the residue was stirred with ice and extracted with dichloromethane. The dichloromethane extract was washed with water, dried and evaporated. The residue was chromatographed on silica (5-15% ethyl acetate/hexane) to give the title compound (2.7 g, 48% yield). MS: m/z=332.

12. Preparation of 6-Amino-2-chloro-5-iodopyrimidine-4-carboxylic acid methyl ester

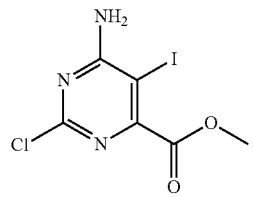

2,6-Dichloro-5-iodopyrimidine-4-carboxylic acid methyl ester (12 g, 36 mmol) was dissolved in dry dimethyl sulfoxide (DMSO; 100 mL) and treated with a stream of ammonia at such a rate when combined with external water bath cooling to keep the temperature in the range of 20-30° C. After 90 min, the ammonia addition was complete and excess ammonia was removed from the mixture by sparging with a stream of nitrogen for 20 min. The mixture was poured into water (200 mL) with stirring and the precipitated product was extracted with ethyl acetate (75 mL) twice. The combined ethyl acetate extracts were washed twice with water (50 mL), once with saturated NaCl solution, dried and evaporated to give the title compound (10 g, 89% yield) that was used without further purification. MS: M/Z=313.

13. Preparation of 6-Amino-2-chloro-5-vinylpyrimidine-4-carboxylic acid methyl ester

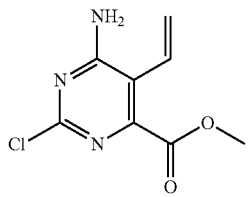

6-Amino-2-chloro-5-iodopyrimidine-4-carboxylic acid methyl ester (10 g, 32 mmol) was dissolved in 1,2-dichloroethane (100 mL), treated with vinyltributylstannane (11.6 mL, 12.6 g, 40 mmol) and sparged with a nitrogen stream for 10 min. Bis(triphenylphosphine)palladium(II) dichloride (1.1 g, 1.6 mmol, 5 mole %) was added and the mixture was heated at reflux under a nitrogen atmosphere for 3 h. The mixture was cooled, stirred with 10% aqueous $KHF_2$ for 30 min, and filtered through diatomaceous earth to remove solids. The filter cake was washed with more 1,2-dichloroethane and ethyl acetate. The combined filtrates were washed with water, washed with saturated $NaHCO_3$, washed with brine, dried, and evaporated. The crude material was chromatographed on silica (5-20% ethyl acetate/dichloromethane containing 2% acetic acid) to give the title compound (4.5 g, 70% yield). This material contained approximately 5% $PPh_3$, but was used without further purification. MS: m/z=213. $^1$H NMR(CDCl$_3$) δ 6.77(dd, 1H), 6.4(br, 2H), 5.70(d, 1H), 5.61 (d, 1H).

14. Preparation of 6-Amino-2-chloropyrimidine-4-carboxylic acid methyl ester

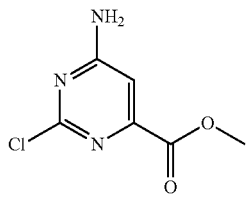

Ammonia was slowly bubbled through a solution of 2,6-dichloro-pyrimidine-4-carboxylic acid methyl ester (20.0 g, 97 mmol, see H. Gershon, *J. Org. Chem.* 1962, 27, 3507-3510 for preparation) in DMSO (100 mL) cooled with an ice bath to maintain the temperature below 70° C. When the temperature of the reaction solution began to decline, no additional ammonia was added. When the temperature of the reaction solution reached 44° C., the ice bath was removed. When the temperature of the reaction solution reached 32° C., the reaction mixture was diluted with 200 mL of water and filtered. The filtered product was washed with water, washed with ethyl acetate, and dried under vacuum to provide the title compound (14.4 g, 79% yield) that was used without further purification. Flash chromatography on silica gel yielded an analytically pure sample of the title compound: $^1$H NMR (DMSO-d$_6$) δ 7.7 (br s, 2H), 7.00 (s, 1H), 3.84 (s, 3H).

15. Preparation of 6-Amino-2-(4-chloro-2-fluoro-3-methoxyphenyl)-pyrimidine-4-carboxylic acid methyl ester

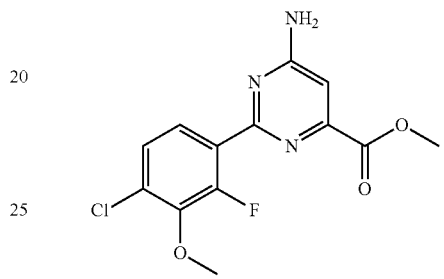

6-Amino-2-chloropyrimidine-4-carboxylic acid methyl ester (2.25 g, 12 mmol, 4-chloro-2-fluoro-3-methoxyphenylboronic acid (3.27 g, 16 mmol), and bis(triphenylphosphine) palladium(II) dichloride (842 mg, 1.2 mmol) were combined in 12 mL of 1,2-dimethoxyethane and 12 mL of water. The reaction mixture was heated at 80° C. for 2 h and the cooled reaction mixture was partitioned between ethyl acetate and water. The organic phase was washed with water, dried, and concentrated under vacuum. The product was purified by flash chromatography on silica gel to yield the title compound (2.0 g, 53.5% yield): mp 188-190° C.: $^1$H NMR (CDCl$_3$) δ 7.66 (dd, 1H), 7.22 (dd, 1H), 7.14 (s, 1H), 5.25 (br s, 2H), 4.0 (s, 3H), 3.99 (s, 3H).

Other compounds prepared by the method of Example 15 include:
6-Amino-2-(4-chloro-2-fluorophenyl)pyrimidine-4-carboxylic acid methyl ester: mp 192-194° C.
6-Amino-2-(4-chlorophenyl)pyrimidine-4-carboxylic acid methyl ester: mp decompose above 195° C.
6-Amino-2-(4-chloro-3-methoxyphenyl)pyrimidine-4-carboxylic acid methyl ester: mp 210-213° C.
6-Amino-2-(4-chloro-2-fluoro-5-methoxyphenyl)pyrimidine-4-carboxylic acid methyl ester: mp 218-220° C.

16. Preparation of 6-Amino-5-bromo-2-(4-chloro-2-fluoro-3-methoxyphenyl)-pyrimidine-4-carboxylic acid methyl ester

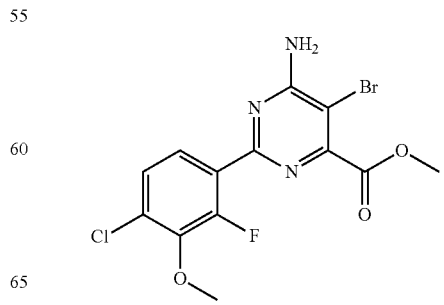

6-Amino-2-(4-chloro-2-fluoro-3-methoxyphenyl)pyrimidine-4-carboxylic acid methyl ester (778 mg, 2.5 mmol) and N-bromosuccinimide (489 mg, 2.75 mmol) were combined in chloroform (10 mL) and heated at reflux for 12 h. The cooled reaction mixture was concentrated and the product was purified by flash chromatography on silica gel to yield the title compound (752 mg, 77% yield): mp 173-175° C.: $^1$H NMR (CDCl$_3$) δ 7.66 (dd, 1H), 7.24 (dd, 1H), 5.73 (br s, 2H), 4.03 (s, 3H), 4.01 (d, 3H).

Other compounds prepared by the method of Example 16 include:

6-Amino-5-bromo-2-(4-chloro-2-fluorophenyl)pyrimidine-4-carboxylic acid methyl ester: mp 186-188° C.

6-Amino-5-bromo-2-(4-chlorophenyl)pyrimidine-4-carboxylic acid methyl ester: mp: decompose above 154° C.

6-Amino-5-bromo-2-(4-chloro-3-methoxyphenyl)pyrimidine-4-carboxylic acid methyl ester: mp 146-151° C.

6-Amino-5-bromo-2-(4-chloro-2-fluoro-5-methoxyphenyl)pyrimidine-4-carboxylic acid methyl ester: mp 197-200° C.

17. Preparation of 6-Amino-2-cyclopropyl-5-methylpyrimidine-4-carboxylic acid ethyl ester (Compound 1)

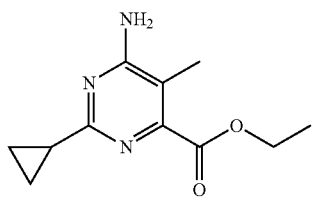 [SMILES: CCOC(=O)c1nc(C2CC2)nc(N)c1C]

6-Amino-5-bromo-2-cyclopropylpyrimidine-4-carboxylic acid ethyl ester (300 mg, 1.05 mmol; see WO 2005/063721 A1 for preparation), tetramethyltin (937 mg, 5.24 mmol), and bis(triphenylphosphine)palladium(II) dichloride (74 mg, 0.105 mmol) were combined in 5 mL of 1,2-dichloroethane and heated in a CEM microwave reactor at 150° C. for 20 min. The resulting reaction mixture was filtered and concentrated. The product was purified by flash chromatography on silica gel (ethyl acetate/hexane gradient) followed by a purification by reverse phase chromatography to yield the title compound (116 mg, 50% yield): mp 130-132° C.: $^1$H NMR (DMSO-d$_6$) δ 6.85 (br s, 2H), 4.27 (q, 2H), 1.94 (s, 3H), 1.87 (m, 1H), 1.28 (t, 3H), 0.84 (d, 4H).

Another compound prepared by the method of Example 17 is:

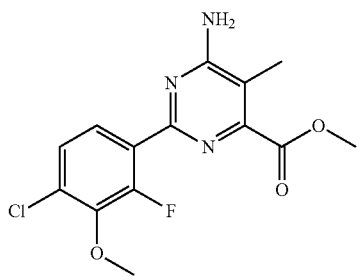 [SMILES: COC(=O)c1nc(-c2ccc(Cl)c(OC)c2F)nc(N)c1C]

6-Amino-2-(4-chloro-2-fluoro-3-methoxyphenyl)-5-methylpyrimidine-4-carboxylic acid methyl ester (Compound 2): mp 168-170° C.: $^1$H NMR (CDCl$_3$) δ 7.60 (m, 1H), 7.21 (m, 1H), 5.21 (br s, 2H), 3.99 (d, 3H), 3.98 (s, 3H), 2.29 (s, 3H).

18. Preparation of 6-Amino-2-(4-chloro-2-fluoro-3-methoxyphenyl)-5-vinylpyrimidine-4-carboxylic acid methyl ester (Compound 3)

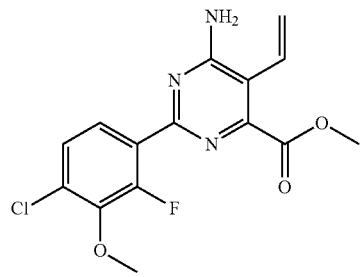

6-Amino-5-bromo-2-(4-chloro-2-fluoro-3-methoxyphenyl)-pyrimidine-4-carboxylic acid methyl ester (1.5 g, 3.84 mmol), tributyl(vinyl)tin (2.436 g, 7.68 mmol), bis(triphenylphosphine)palladium(II) dichloride (0.270 g, 0.384 mmol) were combined in 1,2-dichloroethane (4 mL) and heated at 130° C. for 15 min in a CEM microwave reactor. The cooled reaction mixture was concentrated onto silica gel and purified by flash chromatography on silica gel (ethyl acetate/hexane gradient) to yield the title compound (1.06 g, 82% yield): mp 145-147° C.: $^1$H NMR (CDCl$_3$) δ 7.64 (m, 1H), 7.22 (m, 1H), 6.84 (dd, 1H), 5.68 (m, 2H), 5.43 (br s, 2H), 3.99 (d, 3H), 3.95 (s, 3H).

Other compounds prepared by the method of Example 18 include:

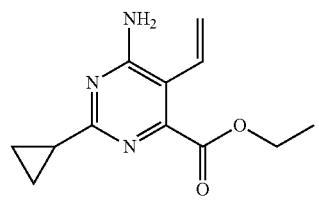 [SMILES: C=Cc1c(N)nc(C2CC2)nc1C(=O)OCC]

6-Amino-2-cyclopropyl-5-vinylpyrimidine-4-carboxylic acid ethyl ester (Compound 4): mp 155-157° C.: $^1$H NMR (CDCl$_3$) δ 6.69 (dd, 1H), 5.57 (dd, 1H), 5.52 (dd, 1H), 5.13 (br s, 1H), 4.39 (1, 2H), 2.07 (m, 1H), 1.38 (t, 3H), 1.07 (m, 2H), 0.96 (m, 1H).

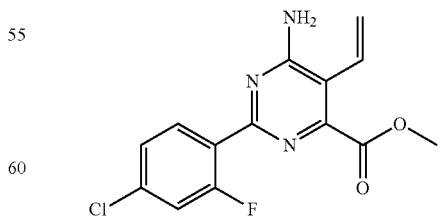

6-Amino-2-(4-chloro-2-fluorophenyl)-5-vinylpyrimidine-4-carboxylic acid methyl ester (Compound 5): mp 137-139° C.: $^1$H NMR (CDCl$_3$) δ 7.96 (m, 1H), 7.20 (m, 2H), 6.83 (dd, 1H), 5.67 (m, 2H), 5.42 (br s, 2H), 3.95 (s, 3H).

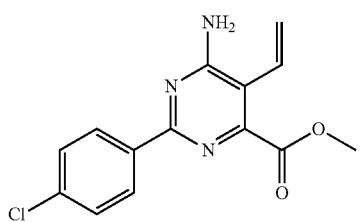 [SMILES: C=Cc1c(N)nc(-c2ccc(Cl)cc2)nc1C(=O)OC]

6-Amino-2-(4-chlorophenyl)-5-vinylpyrimidine-4-carboxylic acid methyl ester (Compound 6): mp 164-167° C.: $^1$H NMR (CDCl$_3$) δ 8.3 (m, 2H), 7.40 (m, 2H), 6.80 (m, 1H), 5.6 (m, 2H), 5.37 (br s, 2H), 3.96 (s, 3H).

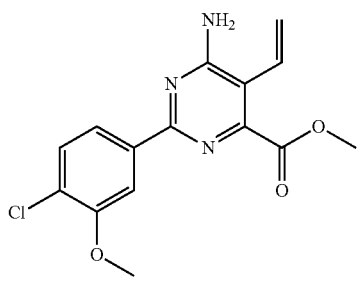 [SMILES: C=Cc1c(N)nc(-c2ccc(Cl)c(OC)c2)nc1C(=O)OC]

6-Amino-2-(4-chloro-3-methoxyphenyl)-5-vinylpyrimidine-4-carboxylic acid methyl ester (Compound 7): mp 144-148° C.: $^1$H NMR (CDCl$_3$) δ 7.92 (m, 2H), 7.40 (d, 1H), 6.78 (m, 1H), 5.6 (m, 2H), 5.39 (br s, 1H), 4.01 (s, 3H), 3.96 (s, 3H).

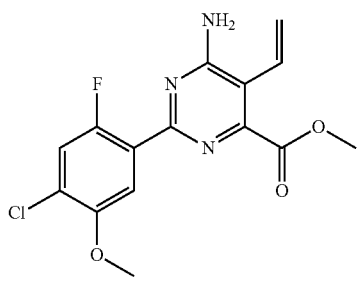 [SMILES: C=Cc1c(N)nc(-c2cc(OC)c(Cl)cc2F)nc1C(=O)OC]

6-Amino-2-(4-chloro-2-fluoro-5-methoxyphenyl)-5-vinylpyrimidine-4-carboxylic acid methyl ester (Compound 8): mp 161-164° C.; $^1$H NMR (DMSO-d$_6$) δ 7.52 (m, 2H), 6.65 (m, 1H), 5.50 (m, 2H), 3.88 (s, 3H), 3.81 (s, 3H).

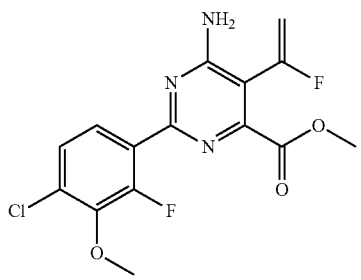

6-Amino-2-(4-chloro-2-fluoro-3-methoxyphenyl)-5-(1-fluorovinyl) pyrimidine-4-carboxylic acid methyl ester (utilized tributyl-(1-fluorovinyl)stannane prepared according to the procedures found in Bull. Chem. Soc. Jpn. 2002, 75(11), 2497-2502) (Compound 9): $^1$H NMR (CDCl$_3$) δ 7.67 (dd, 1H), 7.22 (dd, 1H), 5.52 (br s, 2H), 5.23 (dd, 1H), 4.9 (dd, 1H), 3.99 (d, 3H), 3.95 (s, 3H).

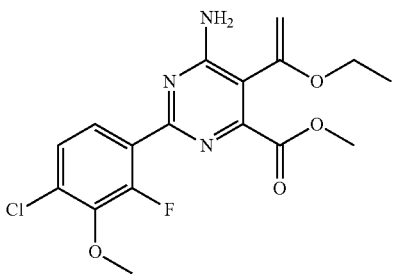 [SMILES: C=C(OCC)c1c(N)nc(-c2ccc(Cl)c(OC)c2F)nc1C(=O)OC]

6-Amino-2-(4-chloro-2-fluoro-3-methoxyphenyl)-5-(1-ethoxyvinyl)pyrimidine-4-carboxylic acid methyl ester (Compound 10): $^1$H NMR (CDCl$_3$) δ 7.62 (dd, 1H), 7.2 (dd, 1H), 5.62 (br s, 2H), 4.5 (dd, 2H), 3.99 (d, 3H), 3.92 (q, 2H), 3.91 (s, 3H), 1.37 (t, 3H).

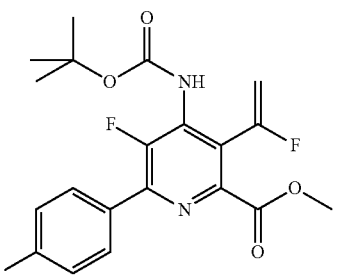

4-tert-Butoxycarbonylamino-6-(4-chlorophenyl)-5-fluoro-3-(1-fluorovinyl)-pyridine-2-carboxylic acid methyl ester (utilized tributyl-(1-fluorovinyl)-stannane prepared according to the procedures found in Bull. Chem. Soc. Jpn. 2002, 75(11), 2497-2502): $^1$H NMR (CDCl$_3$) δ 7.96 (m, 2H), 7.46 (m, 2H), 6.35 (br s, 1H), 5.25 (dd, 1H), 4.85 (dd, 1H), 3.96 (s, 3H). This compound is the starting material for Compound 30 in Example 29.

19. Preparation of 6-Amino-2-(4-chloro-2,3-difluorophenyl)-5-vinyl-pyrimidine-4-carboxylic acid methyl ester (Compound 11)

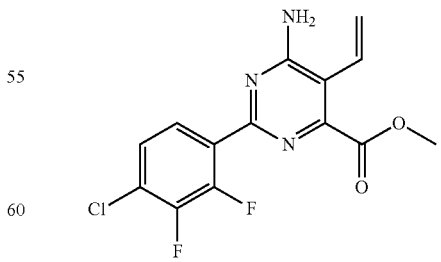

6-Amino-2-chloro-5-vinylpyrimidine-4-carboxylic acid methyl ester (0.6 g, 2.81 mmol), 2-(4-chloro-2,3-difluorophenyl)-4,4,5,5-tetramethyl-[1,3,2]dioxaborolane (1.0 g, 3.65 mmol), bis(triphenylphosphine)-palladium(II) dichloride (197 mg, 0.28 mmol), and cesium fluoride (0.85 g, 5.6 mmol) were combined in 10 mL of 1,2-dimethoxyethane (DME) and 10 mL of water. The reaction mixture was heated in a CEM microwave reactor at 100° C. for 15 min (other temperature/time pairs used in the subsequent examples were 110° C. for 15 min; 150° C. for 5 min). The cooled reaction mixture was diluted with ethyl acetate, washed with water, dried and concentrated. The product was purified by flash chromatography on silica gel (ethyl acetate/hexane gradient) to yield the title compound (0.336 g, 36.7% yield) as a yellow solid (mp 130-132° C.); $^1$H NMR (CDCl$_3$) δ 7.74 (m, 1H), 7.22 (m, 1H), 6.8 (dd, 1H), 5.62-5.7 (m, 2H), 5.67 (m, 1H), 5.42 (br s, 2H), 3.94 (s, 3H).

Other compounds prepared by the method of Example 19 include:

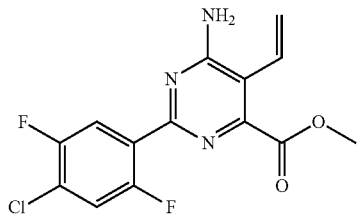 [SMILES: C=Cc1c(N)nc(-c2cc(F)c(Cl)cc2F)nc1C(=O)OC]

6-Amino-2-(4-chloro-2,5-difluorophenyl)-5-vinylpyrimidine-4-carboxylic acid methyl ester (Compound 12): $^1$H NMR (CDCl$_3$) δ 7.84 (dd, 1H), 7.22 (dd, 1H), 6.81 (dd, 1H), 5.62-5.70 (m, 2H), 5.41 (br s, 2H), 3.92 (s, 3H).

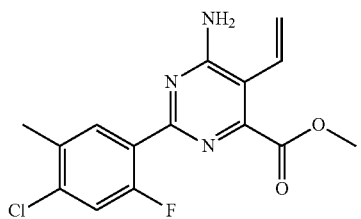

6-Amino-2-(4-chloro-2-fluoro-5-methylphenyl)-5-vinylpyrimidine-4-carboxylic acid methyl ester (Compound 13): $^1$H NMR (CDCl$_3$) δ 7.83 (d, 1H), 7.18 (d, 1H), 6.81 (dd, 1H), 5.6-5.71 (m, 2H), 5.41 (br s, 2H), 3.92 (s, 3H), 2.38 (s, 3H).

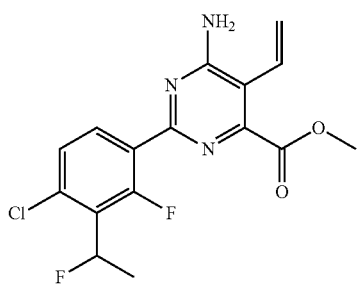 [SMILES: C=Cc1c(N)nc(-c2ccc(Cl)c(C(C)F)c2F)nc1C(=O)OC]

6-amino-2-(4-chloro-2-fluoro-3-(1-fluoroethyl)phenyl)-5-vinylpyrimidine-4-carboxylic acid methyl ester (Compound 14): mp 144-147° C. $^1$H NMR (CDCl$_3$) δ 7.88 (m, 1H), 7.25 (m, 1H), 6.83 (dd, 1H, J=12, 18 Hz), 6.17 (dq, 1H, J=6, 46 Hz), 5.62-5.72 (m, 2H), 5.46 (br s, 2H), 3.95 (s, 3H), 1.79 (ddd, 3H, J=1, 7, 23 Hz).

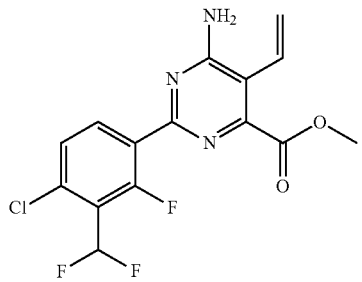 [SMILES: C=Cc1c(N)nc(-c2ccc(Cl)c(C(F)F)c2F)nc1C(=O)OC]

6-Amino-2-(4-chloro-3-difluoromethyl-2-fluorophenyl)-5-vinylpyrimidine-4-carboxylic acid methyl ester (Compound 15): $^1$H NMR (CDCl$_3$) δ 8.07 (m, 1H), 7.31 (br d, 1H, J=8 Hz), 7.03 (dd, 1H, J=1, 53 Hz), 6.83 (dd, 1H, J=12.5, 18 Hz), 5.63-5.73 (m, 2H), 5.44 (br s, 2H), 3.95 (s, 3H).

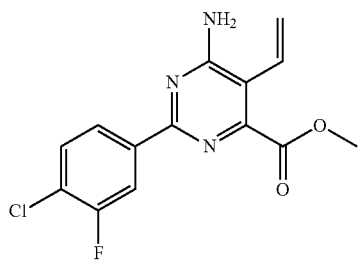 [SMILES: C=Cc1c(N)nc(-c2ccc(Cl)c(F)c2)nc1C(=O)OC]

6-Amino-2-(4-chloro-3-fluorophenyl)-5-vinylpyrimidine-4-carboxylic acid methyl ester (Compound 16): $^1$H-NMR (CDCl$_3$) δ 8.19-8.11(m, 2H) 7.44 (t, J=7.9 Hz, s, 1H), 6.79 (dd, J=11, 6 Hz 1H), 5.68-5.60 (m, 2H), 5.36 (s, 2H), 3.95 (s, 3H).

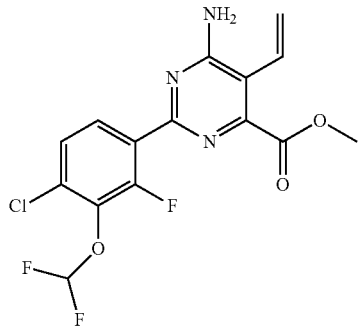 [SMILES: C=Cc1c(N)nc(-c2ccc(Cl)c(OC(F)F)c2F)nc1C(=O)OC]

6-Amino-2-(4-chloro-3-difluoromethoxy-2-fluorophenyl)-5-vinylpyrimidine-4-carboxylic acid methyl ester (Compound 17): $^1$H-NMR (CDCl$_3$) δ 7.87 (t, J=8.6 Hz, 1H) 7.30 (dd, J=6.92, 1.65 Hz, 1H), 6.82 (dd, J=11, 6 Hz, 1H), 6.63 (t, J=73 Hz, 1H), 5.8 (dd, J=7.26, 1.3 Hz, 2H), 5.46(s, 2H), 3.94(s, 3H).

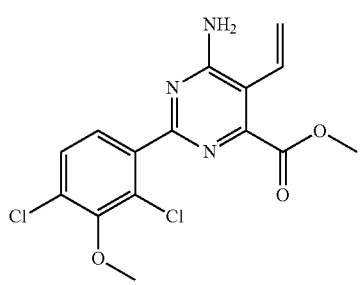 [SMILES: C=Cc1c(N)nc(-c2ccc(Cl)c(OC)c2Cl)nc1C(=O)OC]

6-Amino-2-(2,4-dichloro-3-methoxyphenyl)-5-vinylpyrimidine-4-carboxylic acid methyl ester (Compound 18): $^1$H NMR (CDCl$_3$) δ 7.38 (s, 2H), 6.83 (dd, 1H), 5.63-5.7 (m, 2H), 5.53 (br s, 2H), 3.92 (s, 3H), 3.91 s, 3H).

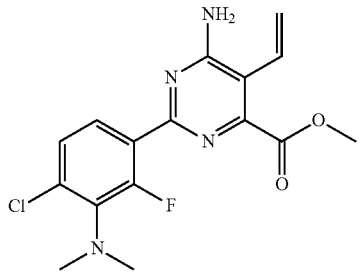 [SMILES: C=Cc1c(N)nc(-c2ccc(Cl)c(N(C)C)c2F)nc1C(=O)OC]

6-Amino-2-(4-chloro-3-dimethylamino-2-fluorophenyl)-5-vinylpyrimidine-4-carboxylic acid methyl ester (Compound 19): $^1$H NMR (CDCl$_3$) δ 7.57 (dd, 1H), 7.2 (dd, 1H), 6.83 (dd, 1H), 5.62-5.70 (m, 2H), 5.42 (br s, 2H), 3.94 (s, 3H), 2.9 (d, 6H).

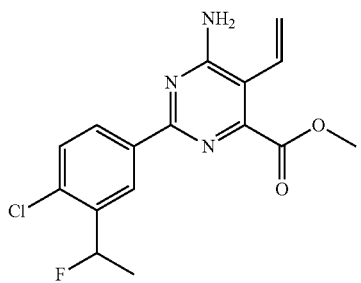 [SMILES: C=Cc1c(N)nc(-c2ccc(Cl)c(C(C)F)c2)nc1C(=O)OC]

6-Amino-2-[4-chloro-3-(1-fluoroethyl)phenyl]-5-vinylpyrimidine-4-carboxylic acid methyl ester (Compound 20): $^1$H NMR (CDCl$_3$) δ 8.53 (m, 1H), 8.26 (m, 1H), 7.40 (m, 1H), 6.78 (dd, 1H), 5.99 (dt, 1H), 5.6-5.66 (m, 2H), 5.35 (br s, 2H), 3.95 (s, 3H), 1.69 (dd, 3H).

20. Preparation of 6-Amino-2-(4-chloro-2-fluoro-3-methoxyphenyl)-5-ethyl-pyrimidine-4-carboxylic acid methyl ester (Compound 21)

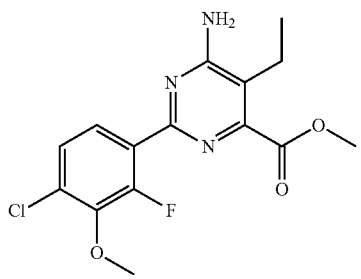 [SMILES: CCc1c(N)nc(-c2ccc(Cl)c(OC)c2F)nc1C(=O)OC]

6-Amino-2-(4-chloro-2-fluoro-3-methoxyphenyl)-5-vinyl-pyrimidine-4-carboxylic acid methyl ester (200 mg, 0.7 mmol) was dissolved in ethanol (10 mL), palladium hydroxide (20% on carbon, 50 mg) was added, and the reaction mixture was stirred under an atmosphere of hydrogen for 4 h. The catalyst was then filtered off, the filtrate concentrated, and the product purified by flash chromatography on silica gel (hexane/ethyl acetate gradient) to yield the title compound (148 mg, 62% yield): mp 144-146° C.: $^1$H NMR (CDCl$_3$) δ 7.61 (m, 1H), 7.20 (m, 1H), 5.19 (br s, 2H), 3.99 (d, 3H), 3.98 (s, 3H), 2.68 (q, 2H), 1.28 (t, 3H).

21. Preparation of 6-Amino-2-(4-chloro-2-fluoro-3-methoxyphenyl)-5-((E)-propenyl)pyrimidine-4-carboxylic acid methyl ester (Compound 22)

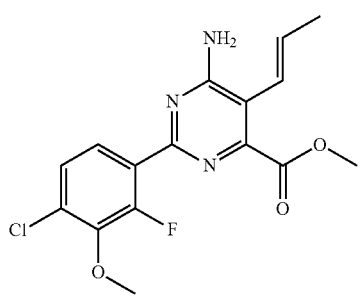 [SMILES: C/C=C/c1c(N)nc(-c2ccc(Cl)c(OC)c2F)nc1C(=O)OC]

6-Amino-5-bromo-2-(4-chloro-2-fluoro-3-methoxyphenyl)-pyrimidine-4-carboxylic acid methyl ester (400 mg, 1.02 mmol), trans-propenyl boronic acid (2132 mg, 1.54 mmol), bis(triphenylphosphine)palladium(II) dichloride (72 mg, 0.1 mmol), and cesium fluoride (311 mg, 2.05 mmol) were combined in 1,2-dimethoxyethane (2 mL) and water (2 mL) and heated at 100° C. for 15 min in a CEM microwave reactor. The cooled reaction mixture was partitioned between ethyl acetate and water; and the organic phase was dried and concentrated. The product was purified by flash chromatography on silica gel (hexane/ethyl acetate gradient) then purified again by reverse phase HPLC to yield the title compound: mp 133-135° C.: $^1$H NMR (CDCl$_3$) δ 7.63 (m, 1H), 7.22 (m, 1H), 6.43 (m, 1H), 6.12 (m, 1H), 5.35 (br s, 2H), 3.99 (d, 3H), 3.94 (s, 3H), 1.94 (dd, 3H).

Another compound prepared by the method of Example 21 is:

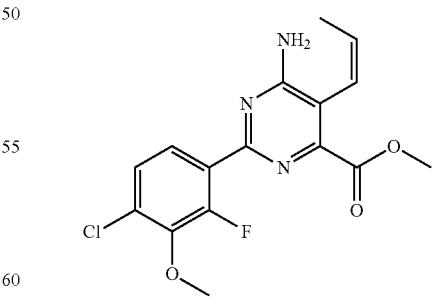

6-Amino-2-(4-chloro-2-fluoro-3-methoxyphenyl)-5-((Z)-propenyl)pyrimidine-4-carboxylic acid methyl ester (Compound 23): mp 91-93° C.: $^1$H NMR (CDCl$_3$) δ 7.67 (m, 1H), 7.22 (m, 1H), 6.38 (m, 1H), 6.07 (m, 1H), 5.32 (br s, 2H), 4.0 (d, 3H), 3.93 (s, 3H).

22. Preparation of 6-Amino-2-(4-chloro-2-fluoro-3-methoxyphenyl)-5-trimethylsilanylethynylpyrimidine-4-carboxylic acid methyl ester

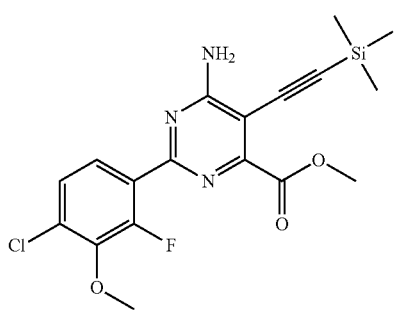 [SMILES: COC(=O)c1nc(-c2ccc(Cl)c(OC)c2F)nc(N)c1C#C[Si](C)(C)C]

6-Amino-5-bromo-2-(4-chloro-2-fluoro-3-methoxyphenyl)-pyrimidine-4-carboxylic acid methyl ester (1.0 g, 2.56 mmol), trimethyl((tributylstannyl)ethynyl)silane (1.98 g, 5.12 mmol), and bis(triphenylphosphine)palladium(II) dichloride (0.18 g, 0.256 mmol) were combined in 1,2-dichloroethane (10 mL) and heated in a CEM microwave reactor at 110° C. for 15 min. The cooled reaction mixture was concentrated under vacuum then purified by flash chromatography on silica gel (dichloromethane/ethyl acetate gradient). A second purification by flash chromatography on silica gel (hexane/ethyl acetate gradient) yielded the title compound (0.829 g, 79% yield): mp 126-128° C.

23. Preparation of 6-Amino-2-(4-chloro-2-fluoro-3-methoxyphenyl)-5-ethynyl-pyrimidine-4-carboxylic acid methyl ester (Compound 24)

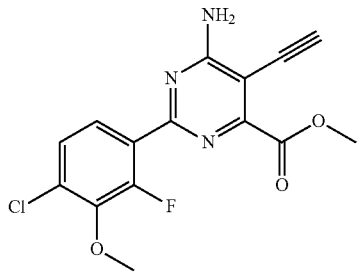 [SMILES: C#Cc1c(N)nc(-c2ccc(Cl)c(OC)c2F)nc1C(=O)OC]

6-Amino-2-(4-chloro-2-fluoro-3-methoxyphenyl)-5-trimethyl-silanylethynylpyrimidine-4-carboxylic acid methyl ester (1.2 g, 2.94 mmol) was dissolved in methanol (20 mL) and potassium carbonate (0.203 g, 1.471 mmol) was added. After 1 h stirring at ambient temperature, the precipitate that formed was filtered off, washed with methanol, dissolved in dichloromethane and washed with water. The organic phase was dried and concentrated to yield the title compound (0.410 g, 41.5% yield): mp 174-176° C.: $^1$H NMR (CDCl$_3$) δ 7.7 (m, 1H), 7.22 (m, 1H), 5.82 (br s, 2H), 4.01 (s, 3H), 4.00 (dd, 3H), 3.85 (s, 1H).

24. Preparation of 4-Amino-6-(4-chlorophenyl)-5-fluoro-3-methylpyridine-2-carboxylic acid methyl ester (Compound 25)

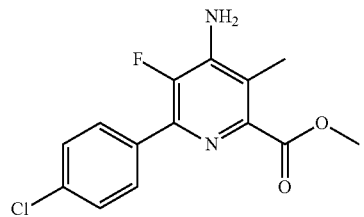 [SMILES: COC(=O)c1nc(-c2ccc(Cl)cc2)c(F)c(N)c1C]

4-Amino-3-chloro-6-(4-chlorophenyl)-5-fluoropyridine-2-carboxylic acid methyl ester (0.400 g, 1.269 mmol), tetramethylstannane (3.41 g, 19.04 mmol), and bis(triphenylphosphine)palladium(II) dichloride (0.089 g, 0.127 mmol) were combined and heated to 130° C. for 25 min in a CEM microwave reactor. The cooled reaction mixture was concentrated onto silica gel and purified by flash chromatography on silica gel (ethyl acetate/hexane gradient) to yield the title compound (0.143 g, 38.2% yield): $^1$H NMR (CDCl$_3$) δ 7.88 (m, 2H), 7.41 (m, 2H), 4.41 (br s, 2H), 3.96 (s, 3H), 2.36 (s, 3H).

25. Preparation of 4-Acetylamino-6-(4-chloro-2-fluoro-3-methoxyphenyl)-3-methylpyridine-2-carboxylic acid methyl ester

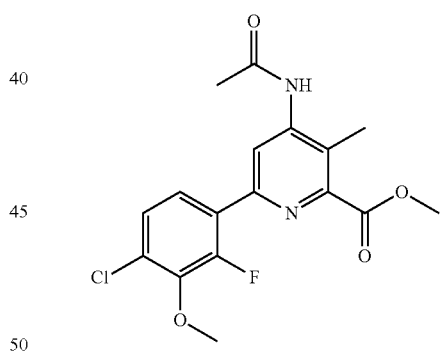

4-Acetylamino-3-chloro-6-(4-chloro-2-fluoro-3-methoxyphenyl)-pyridine-2-carboxylic acid methyl ester (500 mg, 1.29 mmol), tetramethyltin (924 mg, 5.17 mmol), bis(triphenylphosphine)palladium(II) dichloride (91 mg, 0.129 mmol), and tetrabutylammonium triphenyldifluorosilicate (1.395 g, 2.58 mmol) were combined in 2 mL of acetonitrile and heated in a CEM microwave reactor at 110° C. for 15 min. The resulting reaction mixture was filtered and concentrated. This intermediate product was purified by flash chromatography on silica gel (ethyl acetate/hexane gradient) to yield the title compound (419 mg, 88% yield). mp 182-184° C.

26. Preparation of 4-tert-Butoxycarbonylamino-3-chloro-6-(4-chlorophenyl)-5-fluoropyridine-2-carboxylic acid methyl ester

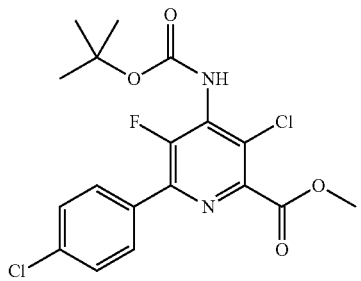 [SMILES: COC(=O)c1nc(-c2ccc(Cl)cc2)c(F)c(NC(=O)OC(C)(C)C)c1Cl]

4-Amino-3-chloro-6-(4-chlorophenyl)-5-fluoropyridine-2-carboxylic acid methyl ester (3 g, 9.5 mmol) was dissolved in dichloromethane (50 mL) and di-tert-butyl dicarbonate (4.6 g, 21 mmol) was added at ambient temperature. After 1 h, the reaction mixture was concentrated and the product was purified by flash chromatography on silica gel (ethyl acetate/hexane gradient). This bis-protected intermediate (3.2 g, 6.2 mmol) was then dissolved in dichloromethane (25 mL) and trifluoroacetic acid (1.42 g, 12.4 mmol) was added. The reaction mixture was stirred for 4 h at ambient temperature then concentrated under vacuum. The product was purified by flash chromatography on silica gel to yield the title compound (2 g, 4.82 mmol, 50.7% yield for the two steps) as a white solid: $^1$H NMR (CDCl$_3$) δ 7.91 (m, 2H), 7.43 (m, 2H), 6.48 (br s, 1H), 4.0 (s, 3H), 1.55 (s, 9H).

27. Preparation of 4-Amino-6-(4-chlorophenyl)-5-fluoro-3-vinylpyridine-2-carboxylic acid methyl ester (Compound 26)

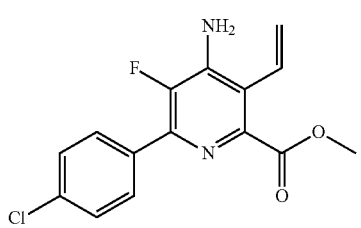 [SMILES: C=Cc1c(C(=O)OC)nc(-c2ccc(Cl)cc2)c(F)c1N]

4-Amino-3-chloro-6-(4-chlorophenyl)-5-fluoropyridine-2-carboxylic acid methyl ester (0.5 g, 1.59 mmol), tributyl(vinyl)tin (1.01 g, 3.17 mmol), bis(triphenylphosphine)palladium(II) dichloride (0.111 g, 0.159 mmol), and tetrabutylammonium triphenyldifluorosilicate (1.71 g, 3.17 mmol) were combined in acetonitrile (3 ml) and heated to 110° C. for 15 min in a CEM microwave reactor. The cooled reaction mixture was concentrated onto silica gel and purified by flash chromatography on silica gel (hexane/ethyl acetate gradient) twice to yield the title compound (46 mg, 5% yield) as an off-white solid, mp 81-83° C. $^1$H NMR (CDCl$_3$) δ 7.9 (m, 1H), 7.43 (m, 1H), 6.89 (dd, 1H), 5.7 (dd, 1H), 5.57 (dd, 1H), 4.72 (br s, 2H), 3.93 (s, 3H).

28. Preparation of 4-Acetylamino-6-(4-chloro-2-fluoro-3-methoxyphenyl)-3-vinylpyridine-2-carboxylic acid methyl ester

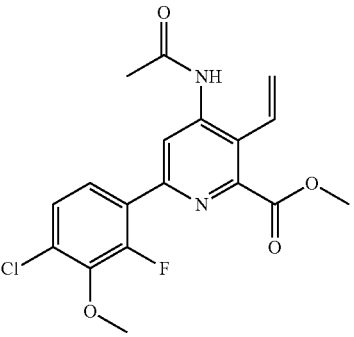 [SMILES: C=Cc1c(NC(C)=O)cc(-c2ccc(Cl)c(OC)c2F)nc1C(=O)OC]

4-Acetylamino-3-chloro-6-(4-chloro-2-fluoro-3-methoxyphenyl)pyridine-2-carboxylic acid methyl ester (0.5 g, 1.29 mmol), tributyl(vinyl)tin (0.821 g, 2.58 mmol), bis(triphenylphosphine)palladium(II) dichloride (0.091 g, 0.129 mmol), and tetrabutylammonium triphenyldifluorosilicate (1.4 g, 2.58 mmol) were combined in acetonitrile (3 ml) and heated to 110° C. for 15 min in a CEM microwave reactor. The cooled reaction mixture was concentrated onto silica gel and purified by flash chromatography on silica gel (ethyl acetate/hexane gradient) to yield the title compound (0.293 g, 60% yield) as a white solid, mp 143-145° C. $^1$H NMR (CDCl$_3$) δ 7.66 (m, 1H), 7.22 (d, 1H), 7.12 (m, 1H), 6.85 (dd, 1H), 5.66 (dd, 1H), 5.57 (dd, 1H), 4.61 (br s, 2H), 3.97 (s, 3H), 3.94 (d, 3H).

Other compounds prepared by the method of Example 28 include:

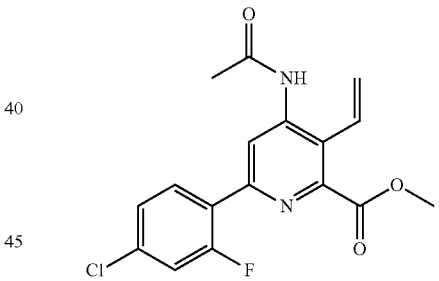

4-Acetylamino-6-(4-chloro-2-fluorophenyl)-3-vinylpyridine-2-carboxylic acid methyl ester.

29. Preparation of 4-Amino-6-(4-chloro-2-fluoro-3-methoxyphenyl)-3-methyl-pyridine-2-carboxylic acid methyl ester (Compound 27)

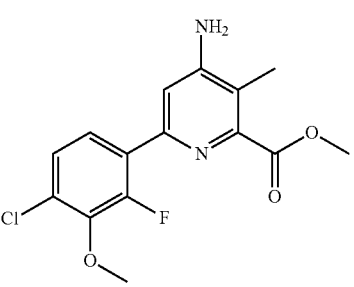 [SMILES: COC(=O)c1nc(-c2ccc(Cl)c(OC)c2F)cc(N)c1C]

4-Acetylamino-6-(4-chloro-2-fluoro-3-methoxyphenyl)-3-methylpyridine-2-carboxylic acid methyl ester (369 mg, 1.0 mmol) was dissolved in methanol (10 mL) and acetyl chloride (1.07 mL, 15 mmol) was added. The reaction mixture was stirred overnight at ambient temperature and concentrated under vacuum. The residue was partitioned between ethyl acetate and aqueous sodium bicarbonate; and the organic phase was dried and concentrated. Purification by flash chromatography on silica gel (dichloromethane/ethyl acetate gradient) followed by a second purification by flash chromatography (hexane/ethyl acetate gradient) yielded the title compound (292 mg, 88% yield) as a white solid, mp 122-125° C. $^1$H NMR (CDCl$_3$) δ 7.65 (m, 1H), 7.26 (s, 1H), 7.1 (m, 1H), 4.35 (br s, 2H), 3.99 (s, 3H), 3.98 (d, 3H), 2.31 (s, 3H).

Other compounds prepared by the method of Example 29 include:

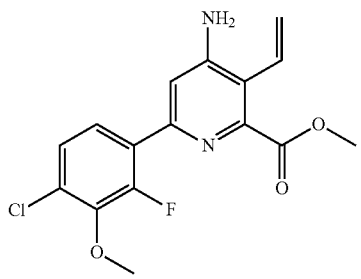 [SMILES: C=Cc1c(N)cc(-c2ccc(Cl)c(OC)c2F)nc1C(=O)OC]

4-Amino-6-(4-chloro-2-fluoro-3-methoxyphenyl)-3-vinylpyridine-2-carboxylic acid methyl ester (Compound 28): mp 118-121° C.: $^1$H NMR (CDCl$_3$) δ 7.67 (m, 1H), 7.24 (d, 1H), 7.13 (m, 1H), 6.86 (dd, 1H), 5.55-5.71 (m, 2H), 4.63 (br s, 2H), 3.99 (s, 3H), 3.94 (s, 3H).

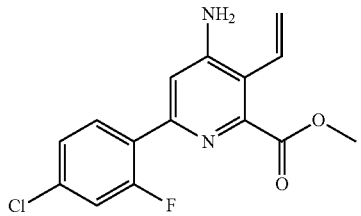 [SMILES: C=Cc1c(N)cc(-c2ccc(Cl)cc2F)nc1C(=O)OC]

4-Amino-6-(4-chloro-2-fluorophenyl)-3-vinylpyridine-2-carboxylic acid methyl ester (Compound 29). $^1$H NMR (CDCl$_3$) δ 8.0 (m, 1H), 7.2 (d, 1H), 7.1 (m, 2H), 6.8 (m, 1H), 5.6 (m, 2 h), 4.6 (s, 2H), 3.9 (s, 3H).

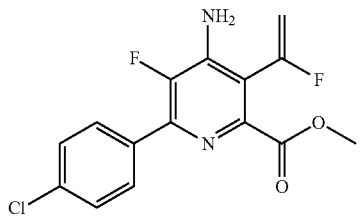 [SMILES: C=C(F)c1c(C(=O)OC)nc(-c2ccc(Cl)cc2)c(F)c1N]

4-Amino-6-(4-chlorophenyl)-5-fluoro-3-(1-fluorovinyl)pyridine-2-carboxylic acid methyl ester (Compound 30): $^1$H NMR (CDCl$_3$) δ 7.9 (m, 2H), 7.43 (m, 2H), 5.27 (dd, 1H), 4.84 (dd, 1H), 4.87 (br s, 2H).

30. Preparation of 4-Acetylamino-6-(4-chloro-2-fluoro-3-methoxyphenyl)-3-trimethylsilanylethynylpyridine-2-carboxylic acid methyl ester

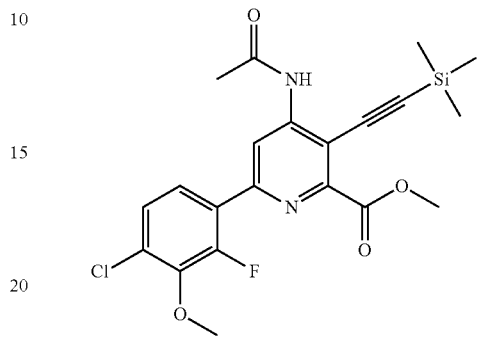

4-Acetylamino-3-chloro-6-(4-chloro-2-fluoro-3-methoxyphenyl)-pyridine-2-carboxylic acid methyl ester (0.8 g, 2.061 mmol), trimethyl((tributylstannyl)ethynyl)silane (1.596 g, 4.12 mmol), and bis(triphenylphosphine)palladium (II) dichloride (0.145 g, 0.206 mmol) were combined in 1,2-dichloroethane (2 mL) and heated in a CEM microwave reactor at 130° C. for 15 min. The cooled reaction mixture was purified by flash chromatography on silica gel (hexane/ethyl acetate gradient) to yield the title compound (0.196 g, 21.1% yield). $^1$H NMR (CDCl$_3$) δ 9.03 (s, 1H), 8.4 (br s, 1H), 7.67 (m, 1H), 7.24 (m, 1H), 4.0 (s, 3H), 3.99 (d, 3H), 2.29 (s, 3H), 0.36 (s, 9H).

31. Preparation of 4-Amino-6-(4-chloro-2-fluoro-3-methoxyphenyl)-3-ethynyl-pyridine-2-carboxylic acid methyl ester (Compound 31)

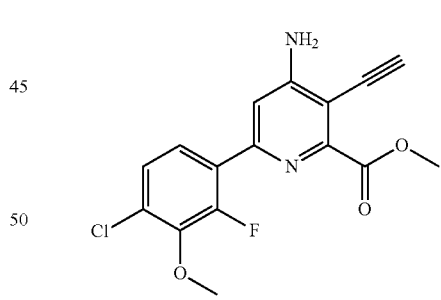

4-Acetylamino-6-(4-chloro-2-fluoro-3-methoxyphenyl)-3-trimethylsilanylethynylpyridine-2-carboxylic acid methyl ester (0.196 g, 0.437 mmol) was suspended in methanol (4.36 mL) and acetyl chloride (0.310 mL, 4.37 mmol) was added. The reaction mixture was stirred overnight at ambient temperature then concentrated to dryness. The residue was dissolved in methanol (4.36 mL) and potassium carbonate (0.121 g, 0.873 mmol) was added. The reaction mixture was stirred at ambient temperature for 2 h, acidified with 2N HCl, and concentrated but not to dryness. The residue was partitioned between ethyl acetate and sodium bicarbonate; and the organic phase was dried and concentrated. The resulting product was purified by flash chromatography on silica gel (ethyl acetate/hexane gradient) to yield the title compound (0.109 g, 74.6% yield) as a yellow solid, mp 167-169° C.: $^1$H NMR (CDCl$_3$) δ 7.7 (m, 1H), 7.24 (s, 1H), 7.18 (m, 1H), 5.08 (br s, 2H), 3.99 (s, 3H), 3.97 (d, 3H), 3.84 (s, 1H).

32. Preparation of 5-Acetyl-6-amino-2-(4-chloro-2-fluoro-3-methoxyphenyl)-pyrimidine-4-carboxylic acid methyl ester (Compound 32)

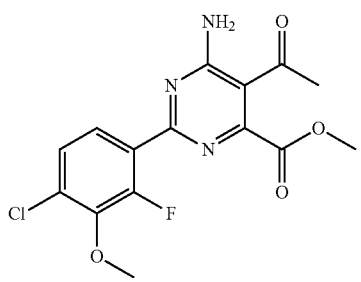 [SMILES: COC(=O)c1nc(-c2ccc(Cl)c(OC)c2F)nc(N)c1C(C)=O]

6-Amino-2-(4-chloro-2-fluoro-3-methoxyphenyl)-5-(1-ethoxy-vinyl)pyrimidine-4-carboxylic acid methyl ester (0.235 g, 0.616 mmol) was dissolved in THF (5 mL) and 2N HCl (0.616 mL, 1.231 mmol) and stirred at ambient temperature for 3 h. The reaction mixture was concentrated, triturated with water, and filtered. The product was washed with methanol and dried under vacuum to yield the title compound (0.205 g, 94% yield): $^1$H NMR (DMSO-d$_6$) δ 7.7 (br s, 2H), 7.63 (dd, 1H), 7.42 (dd, 1H), 3.92 (s, 3H), 3.85 (s, 3H), 2.46 (s, 3H).

33. Preparation of 6-Amino-2-(4-chloro-2-fluoro-3-methoxyphenyl)-5-formyl-pyrimidine-4-carboxylic acid methyl ester (Compound 33)

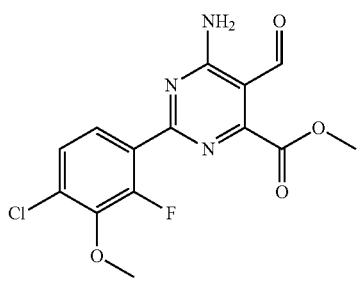

6-Amino-2-(4-chloro-2-fluoro-3-methoxyphenyl)-5-vinyl-pyrimidine-4-carboxylic acid methyl ester (0.500 g, 1.5 mmol) was dissolved in THF (3 mL) and water (3 mL). Osmium tetroxide (4 mg, 0.015 mmol) was added and the reaction mixture was stirred for 2 min. Sodium periodate (0.63 g, 3 mmol) was then added over a period of 2 min. The reaction mixture was stirred for 16 h at ambient temperature then poured into water (150 mL) and extracted with dichloromethane thrice. The combined organic layers were dried, filtered and concentrated to afford the title compound (490 mg, 98% yield) in sufficient purity for subsequent reactions. An analytical sample was obtained by reverse phase chromatography: $^1$H NMR (CDCl$_3$) δ 10.31 (s, 1H), 8.72 (br s, 1H), 7.77 (dd, 1H), 7.23 (m, 1H), 6.03 (br s, 1H), 4.06 (s, 3H), 4.01 (d, 3H).

Another compound prepared by the method of Example 33 is:

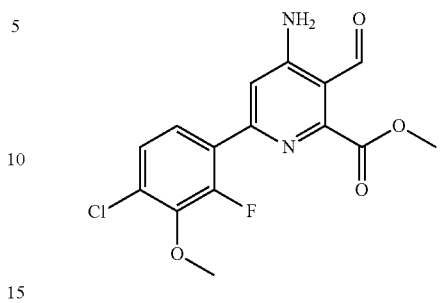

4-Amino-6-(4-chloro-2-fluoro-3-methoxyphenyl)-3-formylpyridine-2-carboxylic acid methyl ester (Compound 34): $^1$H-NMR (CDCl$_3$) δ 10.27 (s,1H), 7.75 (t, J=8.6 Hz, 1H) 7.28 (dd, J=8.6 1.9 Hz, 1H) 7.25 (d, J=1.7 Hz, 1H), 7.12 (m, 2H), 5.3 (s, 2H), 4.03( s, 3H) 3.98 (d, J=1.0 Hz, 3H).

34. Preparation of 6-Amino-2-(4-chloro-2-fluoro-3-methoxy-phenyl)-5-difluoromethylpyrimidine-4-carboxylic acid methyl ester (Compound 35)

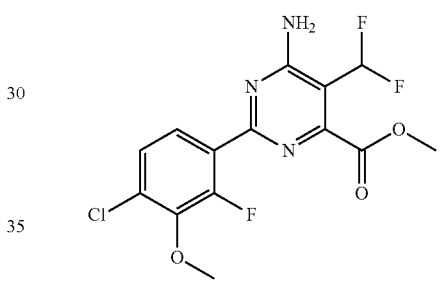

6-Amino-2-(4-chloro-2-fluoro-3-methoxyphenyl)-5-formylpyrimidine-4-carboxylic acid methyl ester (0.120, 0.35 mmol) was dissolved in dichloromethane (5 mL) and diethyl ether (3 mL) with gentle heating. After allowing the solution to cool to ambient temperature, diethylaminosulfur trifluoride (0.5 g, 3.15 mmol) was added and the reaction mixture was gently heated to obtain a clear solution. The reaction mixture was stirred overnight at ambient temperature then quenched with methanol and concentrated under vacuum. The product was purified by flash chromatography on silica gel (ethyl acetate/hexane gradient) to yield the title compound (62 mg, 48% yield): $^1$H NMR (CDCl$_3$) δ 7.69 (dd, 1H), 7.42 (t, 1H), 7.24 (dd, 1H), 5.83 (br s, 2H), 4.02 (s, 3H), 4.0 (d, 3H).

Another compound prepared by the method of Example 34 is:

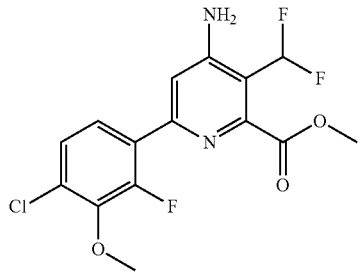 [SMILES: COC(=O)c1nc(-c2ccc(Cl)c(OC)c2F)cc(N)c1C(F)F]

4-Amino-6-(4-chloro-2-fluoro-3-methoxyphenyl)-3-difluoromethylpyridine-2-carboxylic acid methyl ester (Compound 36): ¹H-NMR (CDCl₃) δ 7.76 (t, J=8.2 Hz, 1H) 7.40 (t, J=53.4 Hz, s, 1H) 7.23 (m, 1H), 7.14 (m, 1H), 5.09 (s, 2H), 3.99 (s, 3H), 3.97 (s, 3H).

35. Preparation of 6-Amino-5-((E)-2-bromovinyl)-2-(4-chloro-2-fluoro-3-methoxyphenyl)pyrimidine-4-carboxylic acid methyl ester (Compound 37)

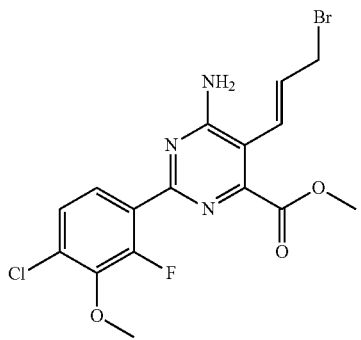 [SMILES: COC(=O)c1nc(-c2ccc(Cl)c(OC)c2F)nc(N)c1/C=C/CBr]

6-Amino-2-(4-chloro-2-fluoro-3-methoxyphenyl)-5-vinylpyrimidine-4-carboxylic acid methyl ester (0.720 g, 2.13 mmol) was dissolved in chloroform (20 mL) and bromine (0.511 g, 3.2 mmol) was added. The reaction mixture was stirred at ambient temperature for 2 h then concentrated under vacuum. The product was dissolved in dichloromethane (20 mL), treated with triethylamine (0.430 g, 4.26 mmol), stirred at ambient temperature for 2 h, and then concentrated under vacuum. The product was purified by flash chromatography on silica gel (dichloromethane/ethyl acetate gradient) to provide the title compound (0.5 g, 56% yield over two steps) as a white solid, mp 171-173° C.: ¹H NMR (CDCl₃) δ 7.66 (dd, 1H), 7.22 (dd, 1H), 7.22 (d, 1H), 6.72 (d, 1H), 5.37 (br s, 2H), 4.0 (s, 3H), 3.97 (s, 3H).

36. Preparation of 6-Amino-2-(4-chloro-2-fluoro-3-methoxyphenyl)-5-((E)-2-methylsulfanylvinyl)pyrimidine-4-carboxylic acid methyl ester (Compound 38)

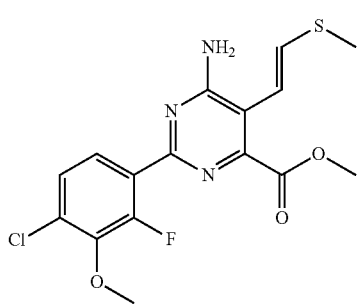 [SMILES: COC(=O)c1nc(-c2ccc(Cl)c(OC)c2F)nc(N)c1/C=C/SC]

6-Amino-5-((E)-2-bromovinyl)-2-(4-chloro-2-fluoro-3-methoxy-phenyl)pyrimidine-4-carboxylic acid methyl ester (0.915 g, 2.196 mmol) was dissolved in DMSO (10 mL) and sodium thiomethoxide (0.169 g, 2.416 mmol) was added. After 30 min at ambient temperature, the reaction mixture was diluted with water and extracted with ethyl acetate. The organic phase was diluted with petroleum ether to decrease the solubility of residual DMSO, washed with water thrice, filtered and concentrated. The product was purified by flash chromatography (hexane/ethyl acetate gradient) to provide the title compound (0.510 g, 60.5% yield) as a yellow solid: ¹H NMR (CDCl₃) δ 7.63 (dd, 1H), 7.19 (dd, 1H), 6.74 (d, 1H), 6.32 (d, 1H), 5.34 (br s, 2H), 3.99 (d, 3H), 3.94 (s, 3H), 2.41 (s, 3H).

37. Preparation of 6-Amino-5-(2-bromo-1-fluoroethyl)-2-(4-chloro-2-fluoro-3-methoxyphenyl)pyrimidine-4-carboxylic acid methyl ester

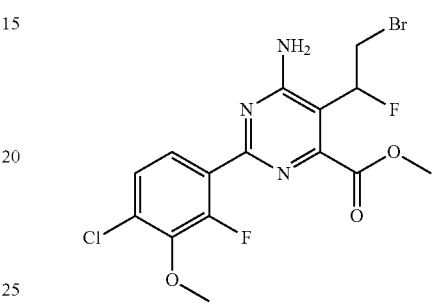

6-Amino-2-(4-chloro-2-fluoro-3-methoxyphenyl)-5-vinyl-pyrimidine-4-carboxylic acid methyl ester (0.611 g, 1.809 mmol) and N-bromosuccinimide (0.386 g, 2.171 mmol) were dissolved in dichloromethane (10 ml) and the reaction mixture was cooled to 0° C. Triethylamine trihydrofluoride (0.884 mL, 5.43 mmol) was then added dropwise and the reaction mixture was allowed to warm to ambient temperature and stirred overnight. Water and additional dichloromethane were added. Sodium bicarbonate (0.760 g, 9.05 mmol) was added in several portions until no further gas evolution was noted. The organic phase was dried and concentrated under vacuum. The product was purified by flash chromatography on silica gel twice (first with dichloromethane/ethyl acetate gradient followed by hexane/ethyl acetate gradient) to provide the title compound (352 mg, 0.806 mmol, 44.6% yield) as a white solid, mp 144-146° C.: ¹H NMR (CDCl₃) δ 7.67 (dd, 1H), 7.23 (dd, 1H), 6.32 (ddd, 1H), 5.77 (br s, 2H), 4.01 (s, 3H), 4.0 (d, 3H), 3.77-3.94 (m, 2H).

38. Preparation of 6-Amino-2-(4-chloro-2-fluoro-3-methoxyphenyl)-5-(1-fluoroethyl)pyrimidine-4-carboxylic acid methyl ester (Compound 39)

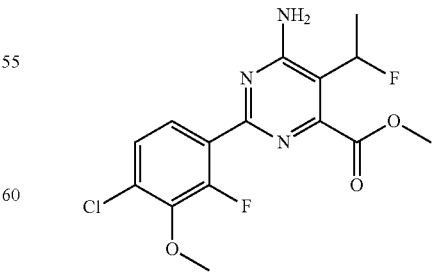

6-Amino-5-(2-bromo-1-fluoroethyl)-2-(4-chloro-2-fluoro-3-methoxyphenyl)pyrimidine-4-carboxylic acid methyl ester (324 mg, 0.742 mmol), tri-n-butyltin hydride (0.396 mL, 1.484 mmol), and 2,2'-azobisisobutyronitrile (3.05 mg, 0.019 mmol) were combined in 1,2-dimethoxyethane (2.5 mL) and heated at 100° C. for 15 min in a CEM microwave reactor. The cooled reaction mixture was concentrated under vacuum then purified by flash chromatography on silica gel (dichloromethane/ethyl acetate gradient). A second purification by flash chromatography on silica gel (hexane/ethyl acetate gradient) yielded the title compound (162 mg, 61.0% yield) as a white solid, mp 150-152° C.: $^1$H NMR (CDCl$_3$) δ 7.64 (dd, 1H), 7.22 (dd, 1H), 6.26 (dq, 1H), 5.73 (br s, 2H), 4.00 (d, 3H), 3.98 (s, 3H), 1.80 (dd, 3H).

39. Preparation of 6-Amino-2-(4-chloro-2-fluoro-3-methoxyphenyl)-5-(1-methoxyethyl)pyrimidine-4-carboxylic acid (Compound 40)

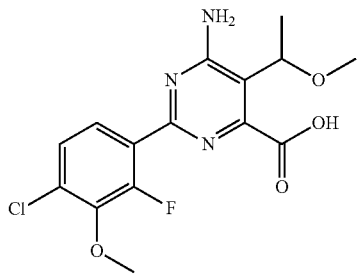 [SMILES: COc1c(Cl)ccc(-c2nc(N)c(C(C)OC)c(C(=O)O)n2)c1F]

6-Amino-2-(4-chloro-2-fluoro-3-methoxyphenyl)-5-(1-fluoroethyl)pyrimidine-4-carboxylic acid methyl ester (0.100 g, 0.280 mmol) was dissolved/suspended in methanol (10 mL) and 2N sodium hydroxide (0.561 mL, 1.121 mmol) was added. The reaction mixture was stirred overnight at ambient temperature, acidified with 2N HCl, and concentrated. The precipitate that formed was filtered, washed with water, and dried to provide the title compound (0.085 g, 85% yield) as a white solid, mp 165-167° C.: $^1$H NMR (DMSO-d$_6$ and drop of D$_2$O) δ 7.60 (dd, 1H), 7.39 (dd, 1H), 4.55 (q, 1H), 3.91 (s, 3H), 3.17 (s, 3H), 1.41 (dd, 3H).

40. Preparation of 6-Amino-2-(4-chloro-2-fluoro-3-methoxyphenyl)-5-vinylpyrimidine-4-carboxylic acid (Compound 41)

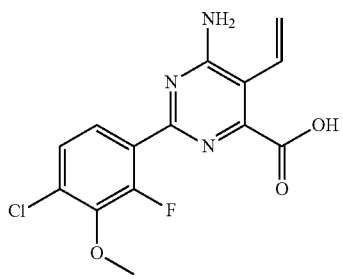 [SMILES: C=Cc1c(N)nc(-c2ccc(Cl)c(OC)c2F)nc1C(=O)O]

6-Amino-2-(4-chloro-2-fluoro-3-methoxyphenyl)-5-vinylpyrimidine-4-carboxylic acid methyl ester (200 mg, 0.59 mmol) was dissolved in methanol (15 mL) and 2N sodium hydroxide (1 mL, 2 mmol) was added. The reaction mixture was stirred at ambient temperature for 2 h, acidified with a slight excess of 2N HCl, and concentrated. The crystals that formed were filtered off, washed with water, washed with diethyl ether, and dried under vacuum to yield the title compound (136 mg, 71% yield): mp 167-168° C.: $^1$H NMR (DMSO-d$_6$ and drop of D$_2$O) δ 7.62 (m, 1H), 7.43 (m, 1H), 6.65 (dd, 1H), 5.67 (m, 2H), 3.92 (d, 3H).

Other compounds prepared by the method of Example 40 include:

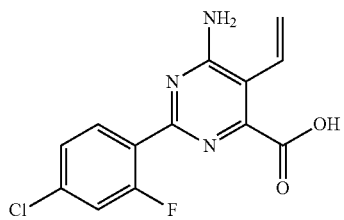 [SMILES: C=Cc1c(N)nc(-c2ccc(Cl)cc2F)nc1C(=O)O]

6-Amino-2-(4-chloro-2-fluorophenyl)-5-vinylpyrimidine-4-carboxylic acid (Compound 42): mp 167-169° C.: $^1$H NMR (DMSO-d$_6$ and drop of D$_2$O) δ 7.91 (m, 1H), 7.51 (m, 1H), 7.40 (m, 1H), 6.65 (dd, 1H), 5.58 (m, 2H).

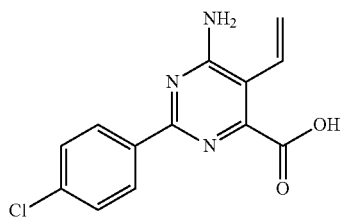 [SMILES: C=Cc1c(N)nc(-c2ccc(Cl)cc2)nc1C(=O)O]

6-Amino-2-(4-chlorophenyl)-5-vinylpyrimidine-4-carboxylic acid (Compound 43): $^1$H NMR (DMSO-d$_6$) δ 13.6 (bs, 1H), 8.26 (d, 2H), 7.53 (d, 2H), 7.19 (bs, 2H), 6.66 (m, 1H), 5.54 (m, 2H). 5.63 (dd, 1H), 5.56 (dd, 1H).

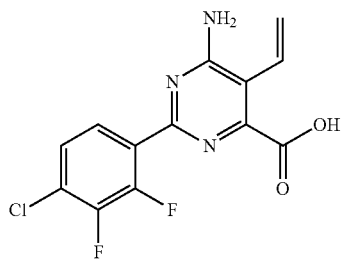 [SMILES: C=Cc1c(N)nc(-c2ccc(Cl)c(F)c2F)nc1C(=O)O]

6-amino-2-(4-chloro-2,3-difluorophenyl)-5-vinylpyrimidine-4-carboxylic acid (Compound 44): mp 170-172° C.: $^1$H NMR (DMSO-d$_6$ and drop of D$_2$O) δ 7.76 (m, 1H), 7.51 (m, 1H), 6.63 (dd, 1H), 5.52-5.61 (m, 2H).

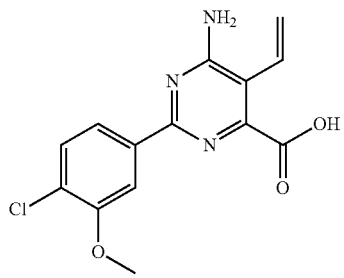 [SMILES: C=Cc1c(N)nc(-c2ccc(Cl)c(OC)c2)nc1C(=O)O]

6-Amino-2-(4-chloro-3-methoxyphenyl)-5-vinylpyrimidine-4-carboxylic acid (Compound 45): $^1$H NMR (DMSO-d$_6$) δ 7.96 (m, 1H), 7.88 (m, 1H), 7.52 (m, 1H), 7.20 (br s, 2H), 6.65 (dd, 1H), 5.48-5.61 (m, 2H), 3.93 (s, 3H).

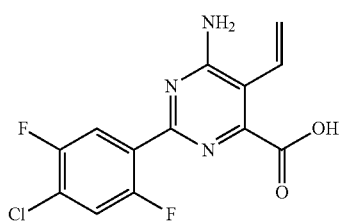 [SMILES: C=Cc1c(N)nc(-c2cc(F)c(Cl)cc2F)nc1C(=O)O]

6-Amino-2-(4-chloro-2,5-difluorophenyl)-5-vinylpyrimidine-4-carboxylic acid (Compound 46): ¹H NMR (CDCl₃ plus DMSO-d₆) δ 7.79 (dd, 1H), 7.07 (dd, 1H), 6.82 (dd, 1H), 6.02 (br s, 2H), 5.55-5.57 (m, 2H).

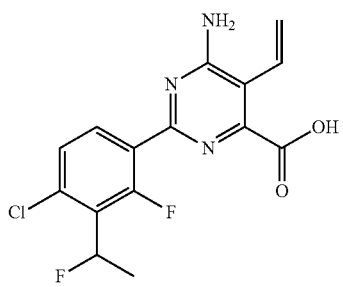 [SMILES: C=Cc1c(N)nc(-c2ccc(Cl)c(C(C)F)c2F)nc1C(=O)O]

6-Amino-2-(4-chloro-2-fluoro-3-(1-fluoroethyl)phenyl)-5-vinylpyrimidine-4-carboxylic acid (Compound 47): mp 150-153° C. ¹H NMR (300 MHz, DMSO-d₆) δ 7.86 (br t, 1H, J=8 Hz), 7.46 (br d, 1H, J=8 Hz), 7.27 (br s, 2H), 6.65 (dd, 1H, J=12, 18 Hz), 6.16 (dq, 1H, J=6, 46 Hz), 5.49-5.65 (m, 2H), 1.73 (dd, 3H, J=7, 23 Hz).

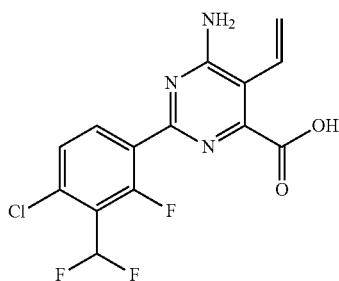 [SMILES: C=Cc1c(N)nc(-c2ccc(Cl)c(C(F)F)c2F)nc1C(=O)O]

6-Amino-2-(4-chloro-3-difluoromethyl-2-fluorophenyl)-5-vinylpyrimidine-4-carboxylic acid (Compound 48): ¹H NMR (DMSO-d₆) δ 8.06 (t, 1H, J=8 Hz), 7.57 (d, 1H, J=8 Hz), 7.13-7.43 (m, 4H), 6.66 (dd, 1H, J=11, 17 Hz), 5.51-5.67 (m, 2H).

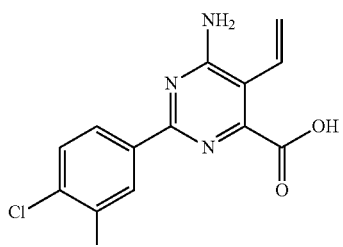

6-Amino-2-(4-chloro-3-fluorophenyl)-5-vinylpyrimidine-4-carboxylic acid (Compound 49): ¹H-NMR (DMSO-d₆) δ 8.17 (m, 2H,) 7.55 (m, 1H), 6.76 (dd, J=11, 6 Hz, 1H), 5.64-5.58 (m, 2H).

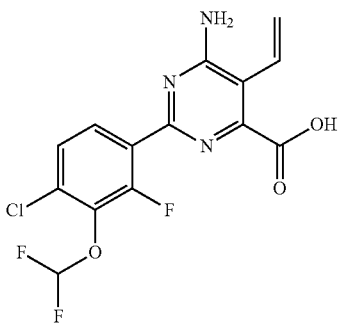 [SMILES: C=Cc1c(N)nc(-c2ccc(Cl)c(OC(F)F)c2F)nc1C(=O)O]

6-Amino-2-(4-chloro-3-difluoromethoxy-2-fluorophenyl)-5-vinylpyrimidine-4-carboxylic acid (Compound 50): ¹H-NMR (DMSO-d₆) δ 13.61 (s, 1H) 7.85 (t, J=8 Hz, 1H), 7.53 (dd, J=7, 1.7 Hz, 1H), 7.29 (bs, 2H), 7.23 (t, J=72 Hz,1H), 6.62 (dd, J=11, 6 Hz, 1H), 5.61-5.49(m, 2H).

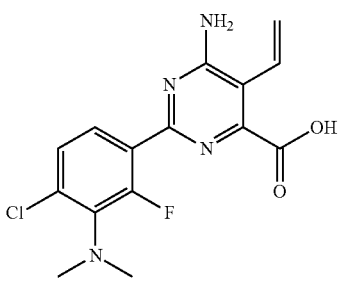 [SMILES: C=Cc1c(N)nc(-c2ccc(Cl)c(N(C)C)c2F)nc1C(=O)O]

6-Amino-2-(4-chloro-3-dimethylamino-2-fluorophenyl)-5-vinylpyrimidine-4-carboxylic acid (Compound 51): ¹H NMR (DMSO-d₆ plus drop of D₂O) δ 7.55 (dd, 1H), 7.34 (dd, 1H), 6.63 (dd, 1H), 5.51-5.62 (m, 2H), 2.81 (d, 6H).

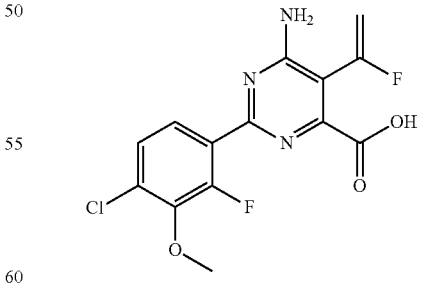

6-Amino-2-(4-chloro-2-fluoro-3-methoxyphenyl)-5-(1-fluorovinyl)pyrimidine-4-carboxylic acid (Compound 52): ¹H NMR (DMSO-d₆ and drop of D₂O) δ 7.62 (dd, 1H), 7.42 (dd, 1H), 5.23 (dd, 1H), 4.94 (dd, 1H), 3.92 (s, 3H).

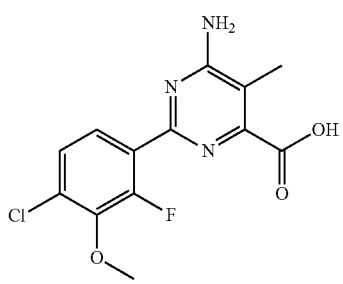

6-amino-2-(4-chloro-2-fluoro-3-methoxyphenyl)-5-methylpyrimidine-4-carboxylic acid (Compound 53): mp 201-203° C.: ¹H NMR (DMSO-d₆ and drop of D₂O) δ 7.57 (m, 1H), 7.38 (m, 1H), 2.11 (s, 3H).

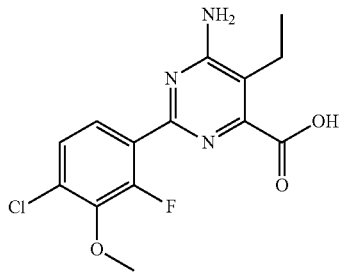 [SMILES: CCc1c(N)nc(-c2ccc(Cl)c(OC)c2F)nc1C(=O)O]

6-Amino-2-(4-chloro-2-fluoro-3-methoxyphenyl)-5-ethylpyrimidine-4-carboxylic acid (Compound 54): ¹H NMR (DMSO-d₆) δ 7.59 (dd, 1H), 7.37 (dd, 1H), 7.18 (br s, 2H), 3.9 (s, 3H), 2.56 (q, 2H), 1.08 (t, 3H).

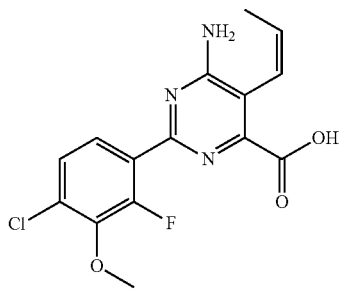 [SMILES: C/C=C\c1c(N)nc(-c2ccc(Cl)c(OC)c2F)nc1C(=O)O]

6-Amino-2-(4-chloro-2-fluoro-3-methoxyphenyl)-5-((Z)-propenyl)pyrimidine-4-carboxylic acid (Compound 55): ¹H NMR (DMSO-d₆ and drop of D₂O) δ 7.63 (m, 1H), 7.40 (m, 1H), 6.17 (dd, 1H), 5.94 (m, 1H), 1.52 (dd, 3H).

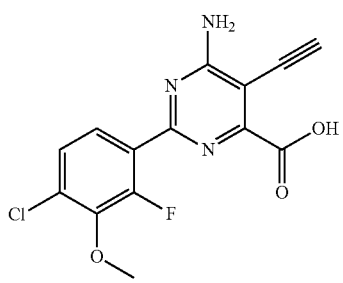 [SMILES: C#Cc1c(N)nc(-c2ccc(Cl)c(OC)c2F)nc1C(=O)O]

6-Amino-2-(4-chloro-2-fluoro-3-methoxyphenyl)-5-ethynylpyrimidine-4-carboxylic acid (Compound 56): ¹H NMR (DMSO-d₆ and drop of D₂O) δ 7.67 (m, 1H), 7.43 (m, 1H), 4.79 (s, 1H), 3.92 (s, 3H).

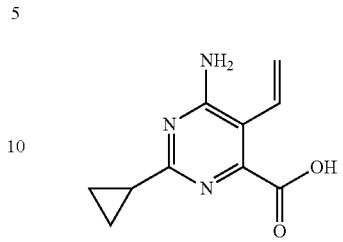

6-amino-2-cyclopropyl-5-vinylpyrimidine-4-carboxylic acid (Compound 57): mp 187-189° C.: ¹H NMR (DMSO-d₆) δ 7.7 (br s, 2H), 7.1 (dd, 1H), 5.92-6.07 (m, 2H), 2.49 (m, 1H), 1.47 (m, 4H).

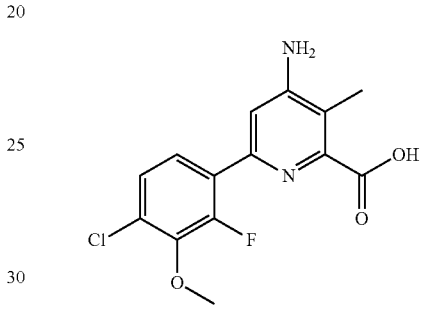

4-Amino-6-(4-chloro-2-fluoro-3-methoxyphenyl)-3-methylpyridine-2-carboxylic acid (Compound 58): ¹H NMR (DMSO-d₆ and drop of D₂O) δ 7.52 (m, 1H), 7.43 (m, 1H). 3.93 (s, 3H), 2.2 (s, 3H).

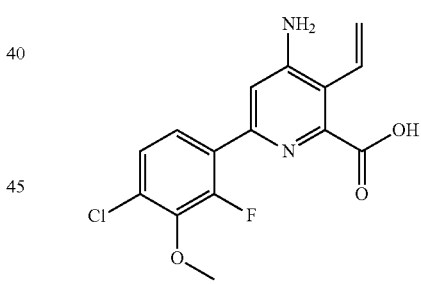

4-Amino-6-(4-chloro-2-fluoro-3-methoxyphenyl)-3-vinylpyridine-2-carboxylic acid (Compound 59): ¹H NMR (DMSO-d₆) δ 7.62 (m, 1H), 7.40 (dd, 1H), 7.10 (d, 1H), 6.70 (dd, 1H), 6.41 (br s, 2H), 5.45-5.57 (m, 2H), 3.92 (d, 3H).

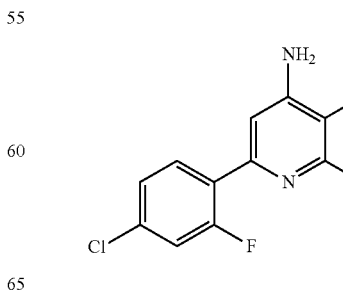

4-Amino-6-(4-chloro-2-fluorophenyl)-3-vinylpyridine-2-carboxylic acid (Compound 60), mp 209-211° C. ¹H NMR (MeOH-d$_4$) δ 7.65 (m, 1H), 7.46 (m, 2H), 6.96 (d, 1H), 6.76 (dd, 1H), 5.75 (dd, 1H), 4.68 (dd, 1H).

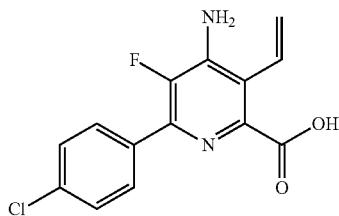

4-Amino-6-(4-chlorophenyl)-5-fluoro-3-vinylpyridine-2-carboxylic acid (Compound 61): $^1$H NMR (DMSO-d$_6$) δ 7.87 (m, 2H), 7.55 (m, 2H), 6.74 (dd, 1H), 5.52-5.56 (m, 2H).

41. Preparation of 6-Amino-2-(4-chloro-2-fluoro-3-methoxyphenyl)-5-vinyl-pyrimidine-4-carboxylic acid butyl ester (Compound 62)

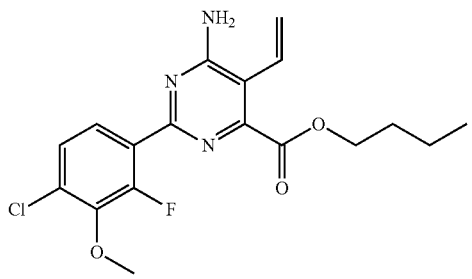

6-Amino-2-(4-chloro-2-fluoro-3-methoxyphenyl)-5-vinyl-pyrimidine-4-carboxylic acid (0.150 g, 0.46 mmol), iodobutane (0.111 g, 0.60 mmol), and lithium carbonate (0.044 g, 0.6 mmol) were combined in DMF (1.5 mL) and heated at 60° C. overnight. The cooled reaction mixture was concentrated and partitioned between ethyl acetate and water. The organic phase was dried and concentrated. The product was purified by flash chromatography on silica gel (ethyl acetate/hexane gradient) to yield the title compound (0.092 g, 52.3% yield): $^1$H NMR (CDCl$_3$) δ 7.65 (dd, 1H), 7.19 (dd, 1H), 7.75 (dd, 1H), 5.62-5.67 (m, 2H), 5.35 (br s, 2H), 4.34 (t, 3H), 3.99 (dd, 3H), 1.74 (m, 2H), 1.45 (m, 2H), 0.97 (t, 3H).

42. Preparation of the triethylamine salt of 6-amino-2-(4-chloro-2-fluoro-3-methoxyphenyl)-5-vinylpyrimidine-4-carboxylic acid (Compound 63)

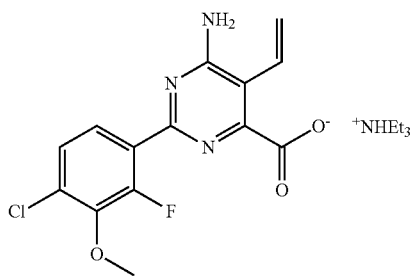

6-Amino-2-(4-chloro-2-fluoro-3-methoxyphenyl)-5-vinyl-pyrimidine-4-carboxylic acid (36 mg) was dissolved in 10 mL of dichloromethane by the addition of 1 mL of triethylamine. The solvent and excess triethylamine were removed under vacuum to yield the title compound in quantitative yield.

43. Preparation of Herbicidal Compositions

In the following illustrative compositions, parts and percentages are by weight.

Emulsifiable Concentrates

Formulation A

|  | WT % |
|---|---|
| Compound 1 | 26.2 |
| Polyglycol 26-3 | 5.2 |
| Nonionic emulsifier-(di-sec-butyl)-phenyl-poly(oxypropylene)block polymer with (oxyethylene). The polyoxyethylene content is about 12 moles. | |
| Witconate P12-20 (Anionic emulsifier-calcium dodecylbenzene sulfonate-60 wt. % active) | 5.2 |
| Aromatic 100 (Xylene range aromatic solvent) | 63.4 |

Formulation B

|  | WT % |
|---|---|
| Compound 3 | 3.5 |
| Sunspray 11N (paraffin oil) | 40.0 |
| Polyglycol 26-3 | 19.0 |
| Oleic acid | 1.0 |
| Xylene range aromatic solvent | 36.5 |

Formulation C

|  | WT % |
|---|---|
| Compound 9 | 13.2 |
| Stepon C-65 | 25.7 |
| Ethomeen T/25 | 7.7 |
| Ethomeen T/15 | 18.0 |
| Xylene range aromatic solvent | 35.4 |

Formulation D

|  | WT % |
|---|---|
| Compound 2 | 30.0 |
| Agrimer Al-10LC (emulsifier) | 3.0 |
| N-methyl-2-pyrrolidone | 67.0 |

Formulation E

| | WT % |
|---|---|
| Compound 18 | 10.0 |
| Agrimul 70-A (dispersant) | 2.0 |
| Amsul DMAP 60 (thickener) | 2.0 |
| Emulsogen M (emulsifier) | 8.0 |
| Attagel 50 (suspension aid) | 2.0 |
| Crop oil | 76.0 |

These concentrates can be diluted with water to give emulsions of suitable concentrations for controlling weeds.

Wettable Powders

Formulation F

| | WT % |
|---|---|
| Compound 44 | 26.0 |
| Polyglycol 26-3 | 2.0 |
| Polyfon H | 4.0 |
| Zeosyl 100 (Precipitated hydrated SiO$_2$) | 17.0 |
| Barden clay + inerts | 51.0 |

Formulation G

| | WT % |
|---|---|
| Compound 58 | 62.4 |
| Polyfon H (sodium salt of lignin sulfonate) | 6.0 |
| Sellogen HR (sodium naphthalene sulfonate) | 4.0 |
| Zeosyl 100 | 27.6 |

Formulation H

| | WT % |
|---|---|
| Compound 59 | 1.4 |
| Kunigel V1 (carrier) | 30.0 |
| Stepanol ME Dry (wetter) | 2.0 |
| Tosnanon GR 31A (binder) | 2.0 |
| Kaolin NK-300 Clay (filler) | 64.6 |

The active ingredient is applied to the corresponding carriers and then these are mixed and ground to yield wettable powders of excellent wettability and suspension power. By diluting these wettable powders with water it is possible to obtain suspensions of suitable concentrations for controlling weeds.

Water Dispersible Granules

Formulation I

| | WT % |
|---|---|
| Compound 57 | 26.0 |
| Sellogen HR | 4.0 |
| Polyfon H | 5.0 |
| Zeosyl 100 | 17.0 |
| Kaolinite clay | 48.0 |

The active ingredient is added to the hydrated silica, which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling weeds.

Granules

Formulation J

| | WT % |
|---|---|
| Compound 50 | 5.0 |
| Celetom MP-88 | 95.0 |

The active ingredient is applied in a polar solvent such as N-methylpyrollidinone, cyclohexanone, gamma-butyrolactone, etc. to the Celetom MP 88 carrier or to other suitable carriers. The resulting granules can be applied by hand, granule applicator, airplane, etc. in order to control weeds.

Formulation K

| | WT % |
|---|---|
| Compound 41 | 1.0 |
| Polyfon H | 8.0 |
| Nekal BA 77 | 2.0 |
| Zinc Stearate | 2.0 |
| Barden Clay | 87.0 |

All materials are blended and ground to a powder then water is added and the clay mixture is stirred until a paste is formed. The mixture is extruded through a die to provide granules of proper size.

Water Soluble Liquids

Formulation L

|  | WT % |
|---|---|
| Compound 62 | 3.67 |
| Monoethanolamine pH buffer | 0.5 |
| Water | 95.83 |

The active ingredient is dissolved in an appropriate amount of water and the additional monoethanolamine is added as a buffer. A water-soluble surfactant may be added. Other aids may be incorporated to improve physical, chemical and/or formulation properties.

44. Evaluation of General Postemergence Herbicidal Activity

Seeds or nutlets of the desired test plant species were planted in Sun Gro MetroMix® 306 planting mixture, which typically has a pH of 6.0 to 6.8 and an organic matter content of about 30 percent, in plastic pots with a surface area of 103 square centimeters. When required to ensure good germination and healthy plants, a fungicide treatment and/or other chemical or physical treatment was applied. The plants were grown for 7-21 days in a greenhouse with an approximate 15 hour photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 mL glass vial and was dissolved in 4 mL of a 97:3 v/v (volume/volume) mixture of acetone and dimethyl sulfoxide (DMSO) to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 v/v (volume/volume) mixture of acetone and dimethyl sulfoxide (DMSO) and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain 1/2X, 1/4X, 1/8X and 1/16X rates of the high rate. Compound requirements are based upon a 12 mL application volume at a rate of 187 L/ha. Formulated compounds were applied to the plant material with an overhead Mandel track sprayer equipped with a 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. After 14 days, the condition of the test plants as compared with that of the untreated plants was determined visually and scored on a scale of 0 to 100 percent where 0 corresponds to no injury and 100 corresponds to complete kill.

Some of the compounds tested, application rates employed, plant species tested, and results are given in Table 1.

TABLE 1

Post-emergent Weed Control

| Compound | Rate g ai/ha | CHEAL | ABUTH | EPHHL | ECHCG | ORYSA |
|---|---|---|---|---|---|---|
| 1 | 280 | 80 | 15 | 100 | 0 | 0 |
| 2 | 280 | 100 | 95 | 100 | 95 | 0 |
| 3 | 70 | 100 | 100 | 100 | 95 | 15 |
| 4 | 140 | 100 | 100 | 100 | 0 | 0 |
| 5 | 140 | 100 | 100 | 100 | 80 | 5 |
| 6 | 280 | 90 | 100 | 70 | 80 | 0 |
| 7 | 280 | 95 | 60 | 70 | 0 | 0 |
| 8 | 280 | 100 | 100 | 50 | 100 | 0 |
| 9 | 140 | 95 | 90 | 100 | 90 | 0 |
| 10 | 280 | 40 | 50 | 75 | 0 | 0 |
| 11 | 70 | 100 | 100 | 100 | 90 | 0 |
| 12 | 140 | 100 | 100 | 50 | 50 | 0 |
| 13 | 280 | 100 | 90 | 60 | 0 | 0 |
| 14 | 70 | 100 | 100 | 100 | 100 | 10 |
| 15 | 140 | 100 | 100 | 100 | 100 | 5 |
| 16 | 140 | 95 | 100 | 80 | 0 | 0 |
| 17 | 280 | 100 | 100 | 100 | 100 | 0 |
| 18 | 140 | 100 | 100 | 40 | 90 | 0 |
| 19 | 280 | 100 | 100 | 100 | 85 | 85 |
| 20 | 280 | 100 | 85 | 100 | 70 | 0 |
| 21 | 140 | 100 | 85 | 100 | 70 | 0 |
| 22 | 70 | 95 | 85 | 100 | 95 | 0 |
| 23 | 70 | 95 | 85 | 100 | 95 | 10 |
| 24 | 140 | 85 | 80 | 85 | 70 | 0 |
| 25 | 280 | 100 | 70 | 100 | 0 | 0 |
| 26 | 140 | 100 | 100 | 90 | 70 | 0 |
| 27 | 280 | 30 | 80 | 100 | 0 | 0 |
| 28 | 280 | 75 | 85 | 90 | 75 | 0 |
| 29 | 280 | 85 | 85 | 75 | 0 | 10 |
| 30 | 140 | 100 | 100 | 90 | 0 | 0 |
| 31 | 140 | 95 | 95 | 100 | 80 | 0 |
| 32 | 280 | 70 | 70 | 100 | 0 | 0 |
| 33 | 229 | 50 | 80 | 100 | 0 | 0 |
| 34 | 280 | 90 | 100 | 95 | 95 | 0 |
| 35 | 280 | 85 | 75 | 90 | 0 | 0 |
| 36 | 280 | 95 | 100 | 95 | 95 | 0 |
| 37 | 280 | 90 | 80 | 90 | 0 | 10 |
| 38 | 280 | 100 | 90 | 100 | 60 | 0 |
| 39 | 140 | 60 | 80 | 85 | 30 | 0 |
| 40 | 280 | 100 | 85 | 100 | 90 | 35 |
| 41 | 70 | 100 | 100 | 100 | 100 | 65 |
| 43 | 280 | 100 | 90 | 100 | 90 | 35 |
| 44 | 70 | 100 | 100 | 100 | 100 | 15 |
| 45 | 280 | 95 | 0 | 60 | 60 | 0 |
| 46 | 140 | 100 | 90 | 95 | 90 | 40 |
| 47 | 70 | 100 | 90 | 100 | 100 | 50 |
| 49 | 140 | 100 | 65 | 100 | NT | 0 |
| 50 | 280 | 100 | 95 | 100 | 100 | 45 |
| 51 | 140 | 100 | 100 | 90 | 95 | 60 |
| 52 | 140 | 95 | 95 | 100 | 90 | 65 |
| 53 | 140 | 100 | 90 | 100 | 90 | 0 |
| 54 | 280 | 100 | 90 | 100 | 90 | 0 |
| 55 | 70 | 100 | 100 | 100 | 100 | 15 |
| 56 | 140 | 95 | 80 | 90 | 75 | 0 |
| 57 | 140 | 100 | 90 | 100 | 30 | 5 |
| 58 | 280 | 50 | 90 | 90 | 50 | 0 |
| 59 | 140 | 100 | 100 | 100 | 100 | 0 |

TABLE 1-continued

Post-emergent Weed Control

| Compound | Rate g ai/ha | CHEAL | ABUTH | EPHHL | ECHCG | ORYSA |
|---|---|---|---|---|---|---|
| 60 | 140 | 100 | 70 | 80 | 35 | 15 |
| 61 | 140 | 100 | 100 | 95 | NT | 50 |
| 62 | 140 | 100 | 100 | 100 | NT | 25 |
| 63 | 70 | 100 | 95 | 100 | 90 | 75 |

CHEAL = lambsquarter (*Chenopodium album*)
ABUTH = velvetleaf (*Abutilon theophrasti*)
EPHHL = wild poinsettia (*Euphorbia heterophylla*)
ECHCG = barnyardgrass (*Echinochloa crus-galli*)
ORYSA = rice (*Oryza sativa*)
NT = not testsed

45. Evaluation of General Preemergence Herbicidal Activity

Seeds of the desired test plant species were planted in a soil matrix prepared by mixing a loam soil (43 percent silt, 19 percent clay, and 38 percent sand, with a pH of about 8.1 and an organic matter content of about 1.5 percent) and sand in a 70 to 30 ratio. The soil matrix was contained in plastic pots with a surface area of 127 square centimeters. When required to ensure good germination and healthy plants, a fungicide treatment and/or other chemical or physical treatment was applied.

A weighed amount, determined by the highest rate to be tested, of each test compound was placed in a 25 mL glass vial and was dissolved in 6 mL of a 97:3 v/v (volume/volume) mixture of acetone and DMSO to obtain concentrated stock solutions. If the test compound did not dissolve readily, the mixture was warmed and/or sonicated. The stock solutions obtained were diluted with 18 mL of a 0.1% v/v aqueous solution of Tween® 20 surfactant to obtain spray solutions containing the highest application rate. Additional application rates were obtained by serial dilution of 12 mL of the high rate solution into a solution containing 3 mL of 97:3 v/v mixture of acetone and DMSO and 9 mL of the 0.1% v/v aqueous solution of Tween® 20 surfactant to obtain 1/2X, 1/4X, 1/8X and 1/16X rates of the high rate. Compound requirements are based upon a 12 mL application volume at a rate of 187 L/ha. Formulated compounds were applied to the soil surface with an overhead Mandel track sprayer equipped with a 8002E nozzles calibrated to deliver 187 L/ha over an application area of 0.503 square meters at a spray height of 18 inches (43 cm) above the soil surface. Control pots were sprayed in the same manner with the solvent blank.

The treated pots and control pots were placed in a greenhouse maintained with an approximate 15 hour photoperiod and temperatures of about 23-29° C. during the day and 22-28° C. during the night. Nutrients and water were added on a regular basis and supplemental lighting was provided with overhead metal halide 1000-Watt lamps as necessary. The water was added by top-irrigation. After 20-22 days, the condition of the test plants that germinated and grew as compared with that of the untreated plants that emerged and grew was determined visually and scored on a scale of 0 to 100 percent where 0 corresponds to no injury and 100 corresponds to complete kill or no emergence.

Some of the compounds tested, application rates employed, plant species tested, and results are given in Table 2.

TABLE 2

Pre-emergent Weed Control

| Compound | Rate g ai/ha | CHEAL | ABUTH | EPHHL | ECHCG | ORYSA |
|---|---|---|---|---|---|---|
| 1 | 140 | 100 | 80 | 100 | 80 | 30 |
| 2 | 140 | 80 | 40 | 95 | 0 | 15 |
| 3 | 140 | 100 | 80 | 100 | 80 | 30 |
| 4 | 280 | 100 | 90 | 100 | 50 | 0 |
| 5 | 140 | 95 | 100 | 90 | 0 | 10 |
| 11 | 70 | 100 | 100 | 100 | 100 | 95 |
| 14 | 140 | 100 | 100 | 100 | 95 | 95 |
| 21 | 140 | 40 | 60 | 80 | 0 | 0 |
| 28 | 140 | 95 | 95 | 100 | 70 | 20 |
| 42 | 140 | 100 | 100 | 100 | 30 | 10 |
| 43 | 140 | 100 | 100 | 100 | 90 | 90 |
| 45 | 140 | 60 | 0 | 0 | 10 | 30 |
| 53 | 140 | 100 | 100 | 100 | 80 | 0 |
| 55 | 140 | 100 | 100 | 100 | 60 | 30 |
| 59 | 140 | 100 | 100 | 100 | 100 | 0 |

CHEAL = lambsquarter (*Chenopodium album*)
ABUTH = velvetleaf (*Abutilon theophrasti*)
EPHHL = wild poinsettia (*Euphorbia heterophylla*)
ECHCG = barnyardgrass (*Echinochloa crus-galli*)
ORYSA = rice (*Oryza sativa*)

What is claimed is:

1. A compound selected from the group consisting of

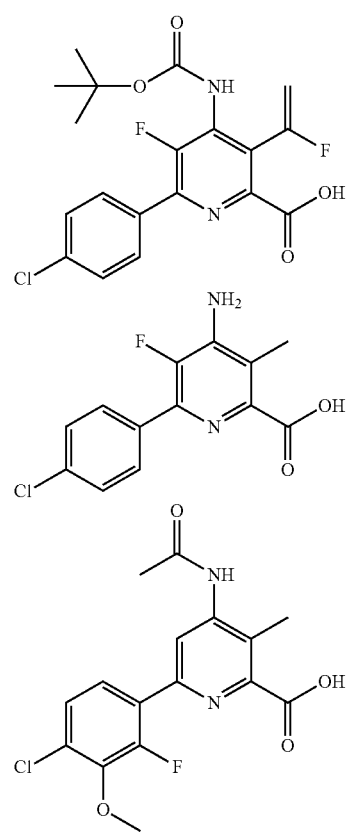

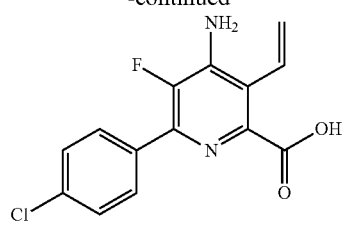
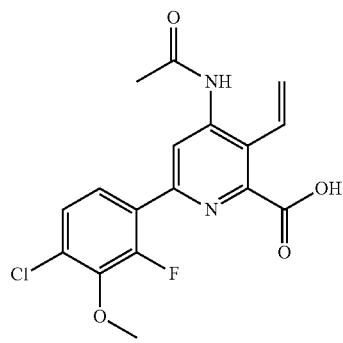
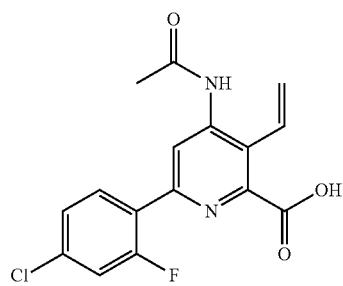
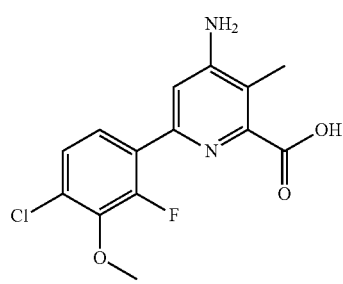 [SMILES: COc1c(Cl)ccc(-c2cc(N)c(C)c(C(=O)O)n2)c1F]
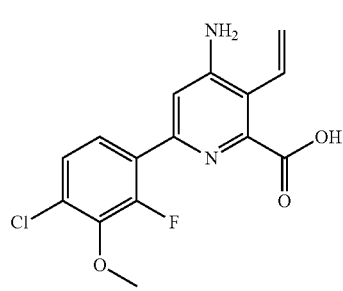 [SMILES: C=Cc1c(N)cc(-c2ccc(Cl)c(OC)c2F)nc1C(=O)O]
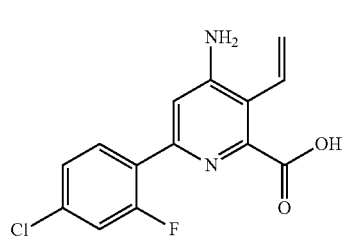 [SMILES: C=Cc1c(N)cc(-c2ccc(Cl)cc2F)nc1C(=O)O]
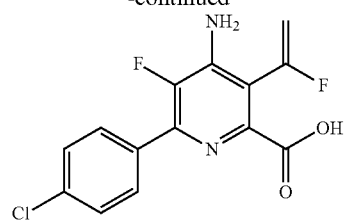
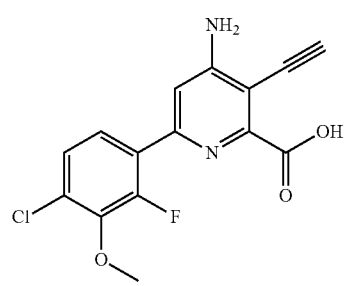
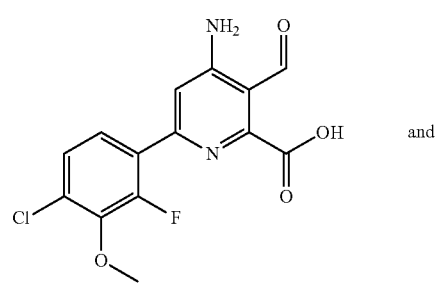
and
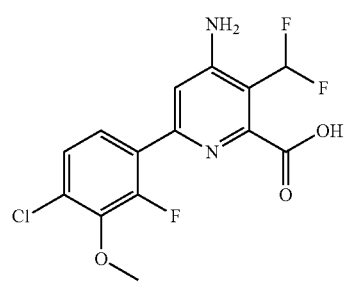
or an agriculturally acceptable salt or ester thereof.
2. The compound of claim 1, wherein the compound is:
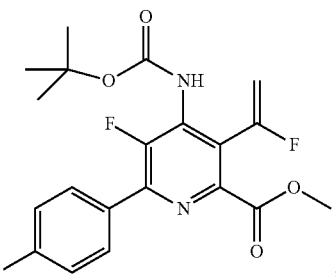
or corresponding carboxylic acid.

3. The compound of claim 1, wherein the compound is:

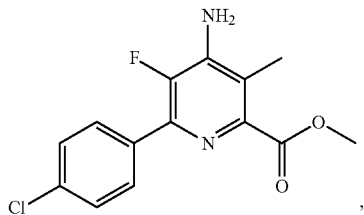 [SMILES: COC(=O)c1nc(-c2ccc(Cl)cc2)c(F)c(N)c1C]

or corresponding carboxylic acid.

4. The compound of claim 1, wherein the compound is:

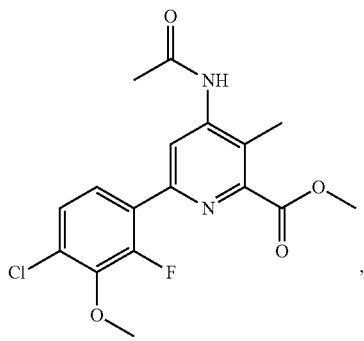 [SMILES: COC(=O)c1nc(-c2ccc(Cl)c(OC)c2F)cc(NC(C)=O)c1C]

or corresponding carboxylic acid.

5. The compound of claim 1, wherein the compound is:

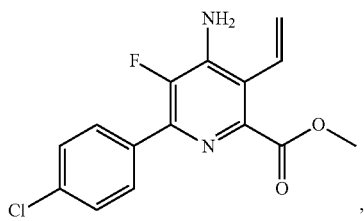 [SMILES: C=Cc1c(C(=O)OC)nc(-c2ccc(Cl)cc2)c(F)c1N]

or corresponding carboxylic acid.

6. The compound of claim 1, wherien the compound is:

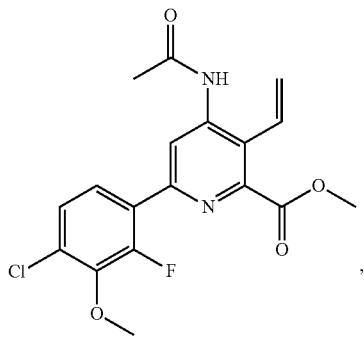 [SMILES: C=Cc1c(NC(C)=O)cc(-c2ccc(Cl)c(OC)c2F)nc1C(=O)OC]

or corresponding carboxylic acid.

7. The compound of claim 1, wherein the compound is:

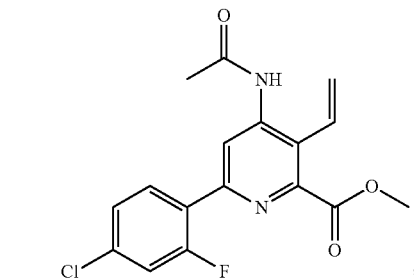

or corresponding carboxylic acid.

8. The compound of claim 1, wherien the compound is:

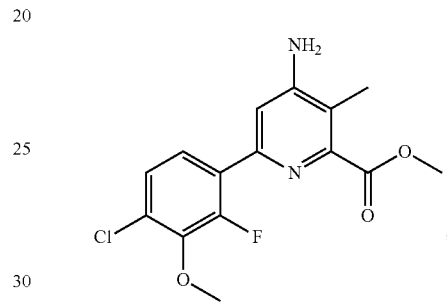

or corresponding carboxylic acid.

9. The compound of claim 1, wherein the compound is:

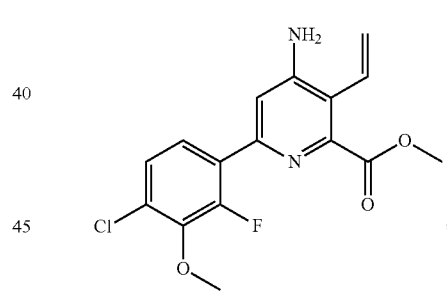

or corresponding carboxylic acid.

10. The compound of claim 1, wherein the compound is:

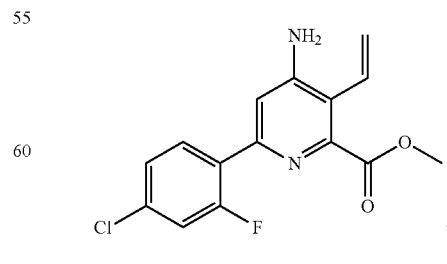

or corresponding carboxylic acid.

11. The compound of claim 1, wherein the compound is:

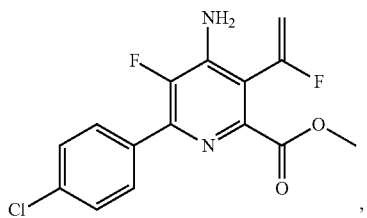 [SMILES: C=C(F)c1c(C(=O)OC)nc(-c2ccc(Cl)cc2)c(F)c1N]

or corresponding carboxylic acid.

12. The compound of claim 1, wherien the compound is:

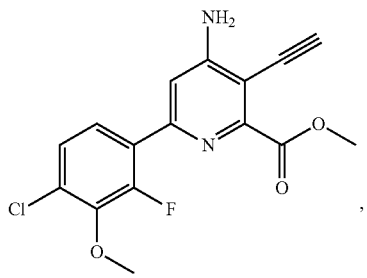 [SMILES: C#Cc1c(N)cc(-c2ccc(Cl)c(OC)c2F)nc1C(=O)OC]

or corresponding carboxylic acid.

13. The compound of claim 1, wherein the compound is

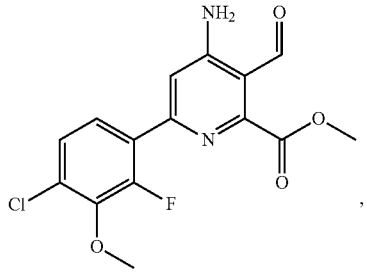 [SMILES: COC(=O)c1nc(-c2ccc(Cl)c(OC)c2F)cc(N)c1C=O]

or corresponding carboxylic acid.

14. The compound of claim 1, wherein the compound is

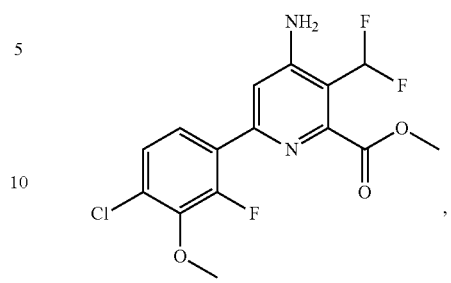

or corresponding carboxylic acid.

15. The compound of claim 1, wherein the compound is

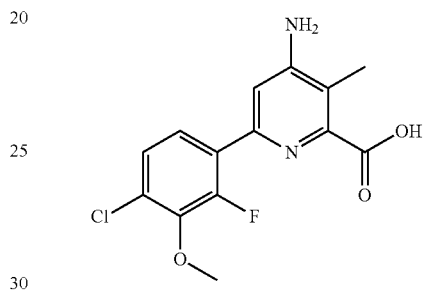

or agriculturally acceptable derivative thereof.

16. A herbicidal composition comprising an herbicidally effective amount of a compound according to claim 1, in a mixture with an agriculturally acceptable adjuvant or carrier.

17. A method of controlling undesirable vegetation which comprises applying an herbicidally effective amount of a compound according to claim 1 where preemergence or postemergence control of undesirable vegetation is desired.

* * * * *